US010426517B2

(12) United States Patent
Langenfeld et al.

(10) Patent No.: US 10,426,517 B2
(45) Date of Patent: **\*Oct. 1, 2019**

(54) CRANIOFACIAL EXTERNAL DISTRACTION APPARATUS

(71) Applicant: DEKA Products Limited Partnership, Manchester, NH (US)

(72) Inventors: Christopher C. Langenfeld, Nashua, NH (US); Stanley B. Smith, III, Raymond, NH (US); David E. Altobelli, Nashua, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,487

(22) Filed: Jul. 11, 2017

(65) Prior Publication Data

US 2017/0303969 A1  Oct. 26, 2017

Related U.S. Application Data

(63) Continuation of application No. 14/191,827, filed on Feb. 27, 2014, now Pat. No. 9,730,731.

(51) Int. Cl.
*A61B 17/66* (2006.01)
*A61B 17/60* (2006.01)
(Continued)

(52) U.S. Cl.
CPC ........... *A61B 17/663* (2013.01); *A61B 17/60* (2013.01); *A61B 17/62* (2013.01); *A61B 17/64* (2013.01);
(Continued)

(58) Field of Classification Search
CPC ......... A61B 17/60; A61B 17/62; A61B 17/64; A61B 17/6433; A61B 17/645;
(Continued)

(56) References Cited

U.S. PATENT DOCUMENTS

| 2,151,458 A | 3/1939 | Allen |
| 2,325,300 A | 7/1943 | Bisnoff |

(Continued)

FOREIGN PATENT DOCUMENTS

| WO | WO2006081254 A2 | 8/2006 |
| WO | WO2013095459 A9 | 6/2013 |

(Continued)

OTHER PUBLICATIONS

Heggie et al., The Role of Distraction Osteogenesis in the Management of Craniofacial Syndromes, Ann Maxillofac. Surg. Jan.-Jun. 2013; 3(1) 4-10 doi: 10.4103/2231-0746.110063, PMCID: PMC3645609, Official Publication of the Indian Academy of Oral and Maxillofacial Surgery.

(Continued)

*Primary Examiner* — Andrew Yang
(74) *Attorney, Agent, or Firm* — James D. Wyninegar, Jr.

(57) ABSTRACT

An external distraction apparatus for performing a craniofacial distraction is disclosed. The external distraction apparatus may comprise a stationary member. The stationary member may be configured to be affixed to a head of a patient. The external distraction apparatus may also comprise laterally disposed distractors. The laterally disposed distractors may extend inferiorly from the stationary member and be moveable relative to the stationary member. The external distraction apparatus may comprise a motor and controller. The motor may be powered with the controller to perform a craniofacial distraction in an automated fashion.

8 Claims, 32 Drawing Sheets

(51) Int. Cl.
*A61B 17/62* (2006.01)
*A61B 17/64* (2006.01)
*A61B 17/00* (2006.01)

(52) U.S. Cl.
CPC ........ *A61B 17/645* (2013.01); *A61B 17/6433* (2013.01); *A61B 17/66* (2013.01); *A61B 2017/00017* (2013.01); *A61B 2017/00022* (2013.01)

(58) Field of Classification Search
CPC .............. A61B 17/66; A61B 17/663; A61B 2017/00017; A61B 2017/00022
See application file for complete search history.

(56) References Cited

U.S. PATENT DOCUMENTS

| | | | |
|---|---|---|---|
| 2,681,058 | A | 6/1954 | Mathues |
| 3,072,118 | A | 1/1963 | Standerwick et al. |
| 3,391,693 | A | 7/1968 | Georgiade et al. |
| 4,973,331 | A * | 11/1990 | Pursley .................. A61B 17/62 606/54 |
| 5,094,229 | A | 3/1992 | Pomatto et al. |
| 5,147,358 | A | 9/1992 | Remmler |
| 6,187,004 | B1 | 2/2001 | Fearon |
| 6,423,019 | B1 | 7/2002 | Papay et al. |
| 6,589,250 | B2 | 7/2003 | Schendel |
| 7,011,642 | B2 | 3/2006 | Greene et al. |
| 7,185,562 | B2 | 3/2007 | Raines, Jr. et al. |
| 7,485,121 | B2 * | 2/2009 | Noon ..................... A61B 17/66 606/90 |
| 7,621,922 | B2 | 11/2009 | Schendel et al. |
| 7,686,836 | B2 | 3/2010 | Johnston et al. |
| 7,862,566 | B2 | 1/2011 | Posnick |
| 7,892,241 | B2 | 2/2011 | Ahmad et al. |
| D728,779 | S | 5/2015 | Sabin et al. |
| D735,319 | S | 7/2015 | Sabin et al. |
| D736,370 | S | 8/2015 | Sabin et al. |
| 9,151,646 | B2 | 10/2015 | Kamen et al. |
| D745,661 | S | 12/2015 | Collins et al. |
| D749,206 | S | 2/2016 | Johnson et al. |
| D751,689 | S | 3/2016 | Peret et al. |
| D751,690 | S | 3/2016 | Peret et al. |
| D752,209 | S | 3/2016 | Peret et al. |
| 9,295,778 | B2 | 3/2016 | Kamen et al. |
| D754,065 | S | 4/2016 | Gray et al. |
| D756,386 | S | 5/2016 | Kendler et al. |
| 9,333,053 | B2 * | 5/2016 | Alyami ................... A61C 7/10 |
| D758,399 | S | 6/2016 | Kendler et al. |
| D760,288 | S | 6/2016 | Kendler et al. |
| D760,289 | S | 6/2016 | Kendler et al. |
| 9,364,394 | B2 | 6/2016 | Demers et al. |
| 9,372,486 | B2 | 6/2016 | Peret et al. |
| D760,782 | S | 7/2016 | Kendler et al. |
| D760,888 | S | 7/2016 | Gill et al. |
| 9,400,873 | B2 | 7/2016 | Kamen et al. |
| D767,756 | S | 9/2016 | Sabin |
| 9,435,455 | B2 | 9/2016 | Peret et al. |
| D768,716 | S | 10/2016 | Kendler et al. |
| 9,465,919 | B2 | 10/2016 | Kamen et al. |
| 9,488,200 | B2 | 11/2016 | Kamen et al. |
| D789,516 | S | 6/2017 | Gill et al. |
| 9,675,756 | B2 | 6/2017 | Kamen et al. |
| 9,677,555 | B2 | 6/2017 | Kamen et al. |
| D792,963 | S | 7/2017 | Gill |
| 9,719,964 | B2 | 8/2017 | Blumberg |
| 9,730,731 | B2 * | 8/2017 | Langenfeld ............ A61B 17/66 |
| 2009/0054897 | A1 | 2/2009 | Gordon et al. |
| 2009/0192514 | A1 * | 7/2009 | Feinberg ............ A61B 17/8004 606/90 |
| 2011/0313789 | A1 | 12/2011 | Kamen et al. |
| 2012/0185267 | A1 | 7/2012 | Kamen et al. |
| 2012/0330312 | A1 * | 12/2012 | Burgherr ................. A61B 17/62 606/54 |
| 2013/0138017 | A1 | 5/2013 | Jundt et al. |
| 2013/0177455 | A1 | 7/2013 | Kamen et al. |
| 2013/0182381 | A1 | 7/2013 | Gray et al. |
| 2013/0184676 | A1 | 7/2013 | Kamen et al. |
| 2013/0188040 | A1 | 7/2013 | Kamen et al. |
| 2013/0191513 | A1 | 7/2013 | Kamen et al. |
| 2013/0197693 | A1 | 8/2013 | Kamen et al. |
| 2013/0204188 | A1 | 8/2013 | Kamen et al. |
| 2013/0272773 | A1 | 10/2013 | Kamen et al. |
| 2013/0281965 | A1 | 10/2013 | Kamen et al. |
| 2013/0297330 | A1 | 11/2013 | Kamen et al. |
| 2013/0310990 | A1 | 11/2013 | Peret et al. |
| 2013/0317753 | A1 | 11/2013 | Kamen et al. |
| 2013/0317837 | A1 | 11/2013 | Ballantyne et al. |
| 2013/0336814 | A1 | 12/2013 | Kamen et al. |
| 2013/0339049 | A1 | 12/2013 | Blumberg, Jr. et al. |
| 2013/0346108 | A1 | 12/2013 | Kamen et al. |
| 2014/0165703 | A1 | 6/2014 | Wilt et al. |
| 2014/0180711 | A1 | 6/2014 | Kamen et al. |
| 2014/0188076 | A1 | 7/2014 | Kamen et al. |
| 2014/0188516 | A1 | 7/2014 | Kamen et al. |
| 2014/0195639 | A1 | 7/2014 | Kamen et al. |
| 2014/0227021 | A1 | 8/2014 | Kamen et al. |
| 2014/0318639 | A1 | 10/2014 | Peret et al. |
| 2014/0343492 | A1 | 11/2014 | Kamen |
| 2015/0002667 | A1 | 1/2015 | Peret et al. |
| 2015/0002668 | A1 | 1/2015 | Peret et al. |
| 2015/0002677 | A1 | 1/2015 | Peret et al. |
| 2015/0033823 | A1 | 2/2015 | Blumberg, Jr. |
| 2015/0154364 | A1 | 6/2015 | Biasi et al. |
| 2015/0157791 | A1 | 6/2015 | Desch et al. |
| 2015/0238228 | A1 | 8/2015 | Langenfeld et al. |
| 2015/0257974 | A1 | 9/2015 | Demers et al. |
| 2015/0314083 | A1 | 11/2015 | Blumberg, Jr. et al. |
| 2015/0332009 | A1 | 11/2015 | Kane et al. |
| 2016/0055397 | A1 | 2/2016 | Peret et al. |
| 2016/0055649 | A1 | 2/2016 | Peret et al. |
| 2016/0061641 | A1 | 3/2016 | Peret et al. |
| 2016/0063353 | A1 | 3/2016 | Peret et al. |
| 2016/0073063 | A1 | 3/2016 | Peret et al. |
| 2016/0084434 | A1 | 3/2016 | Janway et al. |
| 2016/0097382 | A1 | 4/2016 | Kamen et al. |
| 2016/0131272 | A1 | 5/2016 | Yoo et al. |
| 2016/0158437 | A1 | 6/2016 | Biasi et al. |
| 2016/0179086 | A1 | 6/2016 | Peret et al. |
| 2016/0184510 | A1 | 6/2016 | Kamen et al. |
| 2016/0203292 | A1 | 7/2016 | Kamen et al. |
| 2016/0262977 | A1 | 9/2016 | Demers et al. |
| 2016/0319850 | A1 | 11/2016 | Kamen et al. |

FOREIGN PATENT DOCUMENTS

| | | |
|---|---|---|
| WO | WO2013096713 A2 | 6/2013 |
| WO | WO2013096718 A2 | 6/2013 |
| WO | WO2013096722 A2 | 6/2013 |
| WO | WO2013096909 A2 | 6/2013 |
| WO | WO2013176770 A2 | 11/2013 |
| WO | WO2013177357 A1 | 11/2013 |
| WO | WO2014100557 A2 | 6/2014 |
| WO | WO2014100571 A2 | 6/2014 |
| WO | WO2014100658 A1 | 6/2014 |
| WO | WO2014100687 A2 | 6/2014 |
| WO | WO2014100736 A2 | 6/2014 |
| WO | WO2014100744 A2 | 6/2014 |
| WO | WO2014144557 A2 | 9/2014 |
| WO | WO2015017275 A1 | 2/2015 |

OTHER PUBLICATIONS

Imola et al., The Versatility of Distraction Osteogenesis in Craniofacial Surgery, Arch Facial Plast Surg/vol. 4, Jan.-Mar. 2002, pp. 8-19, © 2002 American Medical Association www.archfacial.com, http://archfaci.jamanetwork.com.

Imola et al., Craniofacial Distraction Osteogenesis, Medscape, Apr. 13, 2012, Medscape Reference © 2011 WebMD LLC.

McCarthy, Chapter 12 Principles of Craniofacial Distraction, © 2007 by Lippincott Williams & Wilkins, a Wolters Kluwer business, Grabb and Smith's Plastic Surgery, Sixth Edition by Charles H. Thorne, pp. 96-102.

(56) References Cited

OTHER PUBLICATIONS

Polley et al., Craniomaxillofacial Surgery, RED II System the legend continues, vol. 2.1 Aug. 14, 2013, KLS Maring Group, pp. 1-44.
U.S. Appl. No. 14/191,827, filed Feb. 27, 2014, US20150238228A1
U.S. Appl. No. 14/191,827, filed Feb. 27, 2014.

* cited by examiner

CRANIOFACIAL EXTERNAL DISTRACTION APPARATUS

CROSS-REFERENCE TO RELATED APPLICATION

The present application is a continuation application of U.S. patent application Ser. No. 14/191,827, filed on Feb. 27, 2014 and entitled "Craniofacial External Distraction", now U.S. Publication No. US-2015-0238228-A1, published Aug. 27, 2015.

BACKGROUND

Field of Disclosure

The present disclosure relates to distraction osteogenesis. More specifically, the present disclosure relates to craniofacial distraction osteogenesis.

Background Information

Distraction osteogenesis was first introduced at the turn of the $20^{th}$ century as a process for lengthening long bones. Generally, the process involves performing a corticotomy or osteotomy and then separating (distracting) the resulting pieces of bone such the new bone forms in the gap. The pieces of bone are separated at a rate which does not lead to fibrous non-union as the bone fills in the gap, but also does not allow for bone union until the pieces have been distracted fully along the desired vector. After distraction along the desired vector a consolidation period is generally allotted for during which the bone remodels into a more mature state and the surrounding soft tissues acclimate to their new positions and lengths.

In its infancy, complications such as infection, nerve palsy, joint contractures, etc. were common. The process was refined in the Soviet Union into a viable means of correcting improperly healed fractures and deformities in long bones. Overtime, positive results garnered from the use of distraction osteogenesis in such bones, led to its application in the craniofacial skeleton. Currently, distraction osteogenesis is an established therapeutic option for the correction of a number of craniofacial deformities.

Various devices exist which are used to perform craniofacial distraction osteogenesis. One category of devices is that of external distraction devices. Such devices are manually and intermittently driven. For example, a distractor is adjusted on such devices using screws.

SUMMARY

An embodiment of the present disclosure comprises an external distraction apparatus for performing a craniofacial distraction. The external distraction apparatus may comprise a stationary member. The stationary member a single continuous piece of material and may be configured to be affixed to a head of a patient. At least a portion of the stationary member may be anterior to the head of the patient. The external distraction apparatus may comprise laterally disposed distractors. The laterally disposed distractors may extend inferiorly from the stationary member and be moveable relative to the stationary member.

In some embodiments, the laterally disposed distractors may each be comprised of one or more moveable unit. Each of the moveable units may be moveable relative to the stationary member.

The laterally disposed distractors may each be comprised of a plurality of moveable units. Each of the plurality of moveable units may be moveable relative to the stationary member. At least one of the moveable units may be moveable relative to another of the moveable units. At least one of the moveable units may be a sub unit of a parent moveable unit. The sub unit may move in tandem with the parent moveable unit when the parent movable unit is displaced. The sub unit may also be configured for displacement relative to the parent moveable unit. One of the plurality of moveable units on each of the laterally disposed distractors may be displaceable along a first displacement axis. One of the plurality of moveable units on each of the laterally disposed distractors may be displaceable along a second displacement axis. The second displacement axis may be substantially perpendicular to the first displacement axis. One of the plurality of moveable units on each of the laterally disposed distractors may be displaceable about a pitch axis. The pitch axis may be substantially perpendicular to both the first axis and the second axis. Each of the moveable units may be associated with a displacement means configured to displace the moveable unit. The displacement means may be a manual displacement means or an automated displacement means.

In some embodiments, the laterally disposed distractors may each be comprised of a plurality of moveable units. Each of the moveable units may be moveable relative to the stationary member along or about a displacement axis.

An embodiment of the present disclosure comprises an external distraction apparatus for performing automated craniofacial distraction. The external distraction apparatus may comprise a stationary member configured to be affixed to a head of a patient. The external distraction apparatus may comprise a moveable portion. The moveable portion may be moveable relative to the stationary member. The external distraction apparatus may comprise a motor. The motor may have a drive output configured to move the moveable portion relative to the stationary member. The external distraction apparatus may comprise a controller. The controller may be configured to power the motor on a preprogrammed schedule.

In some embodiments, the controller may be disposed in a separate housing. The separate housing may be in electrical communication with the motor. The controller may be further configured to power the motor to affect a preprogrammed amount of relative movement between the moveable portion and the stationary member. The controller may be configured to put the external distraction apparatus into a sleep state after powering the motor to affect the preprogrammed amount of relative movement.

In some embodiments, the external distraction apparatus may further comprise a first sensor. The first sensor may be arranged to sense relative movement between the moveable portion and the stationary member. The controller may be configured to power the motor until a predetermined amount of relative movement between the moveable portion and the stationary member has been sensed by the first sensor. The first sensor may be a rotary encoder. The rotary encoder may be a magnetic rotary encoder. The external distraction apparatus may further comprise a second sensor. The second sensor may be configured to sense relative movement between the moveable portion and the stationary member. The controller may be configured to compare data from the first sensor and second sensor and place the external distraction apparatus into a fail-safe state in the event that data from the first sensor and second sensor are outside of a predetermined range or proportionality to one another.

In accordance with an embodiment of the present disclosure, a method for performing a craniofacial distraction may comprise affixing a stationary member of an external distraction apparatus to a head of a patient. The method may comprise programming a controller for the external distraction apparatus with a distraction schedule. The method may comprise commanding motor movement with the controller based on the distraction schedule. Each motor movement may cause a predetermined amount of movement of a moveable portion of the apparatus relative to the stationary member.

An embodiment of the present disclosure comprises an external distraction apparatus for performing a craniofacial distraction. The external distraction apparatus may comprise a stationary member. The stationary member may be configured to be affixed to a head of a patient. The external distraction apparatus may comprise a plurality of moveable units. Each of the plurality of moveable units may be moveable relative to the stationary member of the external distraction apparatus. At least two of the plurality of moveable units may be directly coupled to the stationary member.

In some embodiments, the moveable units directly coupled to the stationary member may extend inferiorly from the stationary member. The plurality of moveable units may be disposed laterally on external distraction apparatus. The plurality of moveable units may be divided into sets of moveable units. Each set of moveable units may be disposed on opposing lateral portions of the external distraction apparatus. At least one of the plurality of moveable units may be moveable relative to another of the plurality of moveable units. At least one of the plurality of moveable units may be a sub unit of a parent moveable unit. The sub unit may move in tandem with the parent moveable unit when the parent movable unit is displaced. The sub unit may also be configured for displacement relative to the parent moveable unit. A number of the plurality of moveable units may be displaceable along a first displacement axis. A number of the plurality of moveable units may be displaceable along a second displacement axis. A number of the plurality of moveable units may be displaceable about a pitch axis. Each of the moveable units may be associated with a displacement means configured to displace the moveable unit. The moveable units may each be moveable relative to the stationary member along or about a displacement axis.

An embodiment of the present disclosure comprises an external distraction apparatus for performing a craniofacial distraction. The external distraction apparatus may comprise a stationary member configured to be affixed to a head of a patient. The external distraction apparatus may comprise a moveable portion. The moveable portion may be moveable relative to the stationary member. The external distraction apparatus may comprise a coupling element attached to the moveable portion. The coupling element may be configured to directly couple to a transcutaneous rod such that said coupling element is not moveable relative to the transcutaneous rod. Both linear and moment forces may be applied to the transcutaneous rod through the coupling element.

In some embodiments, the coupling element may be configured to be adjustable such that, without moving the moveable portion, it may couple to a transcutaneous rod which may be in a range of positions.

The coupling element may include an adjustable boom having a longitudinal axis. The adjustable boom may be configured to couple directly to the transcutaneous rod. The adjustable boom may be displaceable axially along the longitudinal axis and displaceable rotationally about the longitudinal axis. The coupling element may include a boom clamp for statically clamping the adjustable boom in a desired orientation. The boom clamp may be included on a linkage, the linkage may be attached to the moveable portion. The boom clamp may be pivotable about a pivot axis. The pivot axis may be perpendicular to the longitudinal axis of the boom. The boom clamp may be configured to be statically clamped in a desired pivotal orientation. The boom clamp may be coupled to a boom clamp mount. The boom clamp mount may be received by a receiving feature in the moveable portion. The boom clamp mount may be displaceable along a longitudinal axis of the receiving feature and rotationally around the longitudinal axis of the receiving feature such that the boom clamp mount may be displaced into a desired orientation. The receiving feature may be a chuck which may clamp the boom clamp mount statically in the desired orientation.

In some embodiments, the coupling element may include a housing. The housing may include an interior volume. The coupling element may include a bearing for the transcutaneous rod. The bearing may extend through the interior volume of the housing. The bearing may be configured to be displaceable within the interior volume in one or more degrees of freedom to accommodate a range of possible spatial orientations for the transcutaneous rod without moving the moveable unit. The bearing may be locked in a desired orientation within the interior volume such that it is no longer displaceable within the interior volume. The interior volume may be at least partially filled with a fusible alloy. The fusible alloy may be a fusible alloy which transitions to a molten state between about 110 degrees and 250 degrees Fahrenheit. The fusible alloy may be an indium bismuth fusible alloy. The fusible alloy may be about 66.3% indium and 33.7% bismuth. The coupling element may include a bearing for the transcutaneous rod. The bearing may extend through the interior volume of the housing. The bearing may be displaceable in one or more degrees of freedom within the interior volume to accommodate a range of possible spatial orientations for the transcutaneous rod without moving the moveable unit when the fusible alloy is in a molten state. The bearing may be locked in place and incapable of movement within the interior volume when the fusible alloy is in a frozen state.

In accordance with an embodiment of the present disclosure a method for performing a craniofacial distraction may comprise affixing a stationary member of an external distraction apparatus to a head of a patient. The method may comprise displacing a first moveable unit along a first displacement axis. The method may comprise displacing a second moveable unit along a second displacement axis. The second displacement axis may be different from the first displacement axis. The second displacement axis may intersect the first displacement axis. The second displacement axis may be perpendicular to the first displacement axis. The method may comprise displacing a third moveable unit. The method may comprise transmitting displacement of the first, second, and third moveable unit to a portion of the craniofacial skeleton to cause distraction of the portion of the craniofacial skeleton.

In some embodiments, displacing the third moveable unit may comprise displacing the third moveable unit about a pitch axis. Displacing the third moveable unit may comprise displacing third moveable unit along a third displacement axis being offset, but parallel to the first displacement axis. Displacement of the first, second, and third moveable unit may be affected by actuating an actuation means. The actuation means may be a manual actuation means, automated actuation means, or a combination thereof. The second displacement axis may be substantially perpendicular to the first displacement axis. Displacing the first moveable unit may cause displacement of the second and third moveable unit along the first displacement axis. Displacing the second moveable unit may cause displacement of the second and third moveable unit relative to the first moveable unit along the second displacement axis. Displacement of the third moveable unit may be relative to both the first moveable unit and second moveable unit. Transmitting displacement of the first, second, and third moveable unit may comprise transmitting displacement through a coupling element directly and statically coupled to a transcutaneous rod which is anchored to the portion of the craniofacial skeleton.

In accordance with an embodiment of the present disclosure, a method for coupling an external distraction apparatus to a transcutaneous rod may comprise affixing a portion of the external distraction apparatus to a head of a patient. The method may comprise adjusting a coupling element included on the external distraction apparatus such that the coupling element intercepts the transcutaneous rod. The method may comprise directly coupling the coupling element to the transcutaneous rod such that the transcutaneous rod and coupling element are incapable of movement relative to one another.

In some embodiments, adjusting the coupling element may comprise heating a fusible alloy which at least partially fills an interior volume of a housing of the coupling element until it becomes molten. Adjusting the coupling element may further comprise displacing, when the fusible alloy is molten, a bearing which extend through the interior volume of the housing of the coupling element into an intercepting position in which the bearing may be slid over the transcutaneous rod. The method may further comprise sliding the bearing over the transcutaneous rod. Directly coupling the coupling element to the transcutaneous rod such that the transcutaneous rod and coupling element are incapable of movement relative to one another may comprise allowing the fusible alloy to cool to a frozen state.

In some embodiments, adjusting the coupling element may comprise adjusting an adjustable boom by displacing the boom longitudinally about a longitudinal axis of the boom and rotationally around the longitudinal axis of the boom. Adjusting the coupling element may further comprise clamping the adjustable boom in a desired orientation with a boom clamp. Adjusting the coupling element may further comprise pivoting the boom clamp about a pivot axis. The pivot axis may be perpendicular to the longitudinal axis of the boom. Adjusting the coupling element may further comprise clamping the boom clamp in a desired pivotal orientation. Adjusting the coupling element may further comprise displacing a boom clamp mount longitudinally along a longitudinal axis of a receiving feature of the external distraction apparatus in which the boom clamp mount is received, and rotationally around the longitudinal axis of the receiving feature. The boom clamp may be coupled to the boom clamp mount. Adjusting the coupling element may further comprise chucking the boom clamp mount into place within the receiving feature such that the boom clamp mount is clamped in a desired orientation within the receiving feature.

BRIEF DESCRIPTION OF THE DRAWINGS

These and other aspects will become more apparent from the following detailed description of the various embodiments of the present disclosure with reference to the drawings wherein.

DETAILED DESCRIPTION

Figure 1:
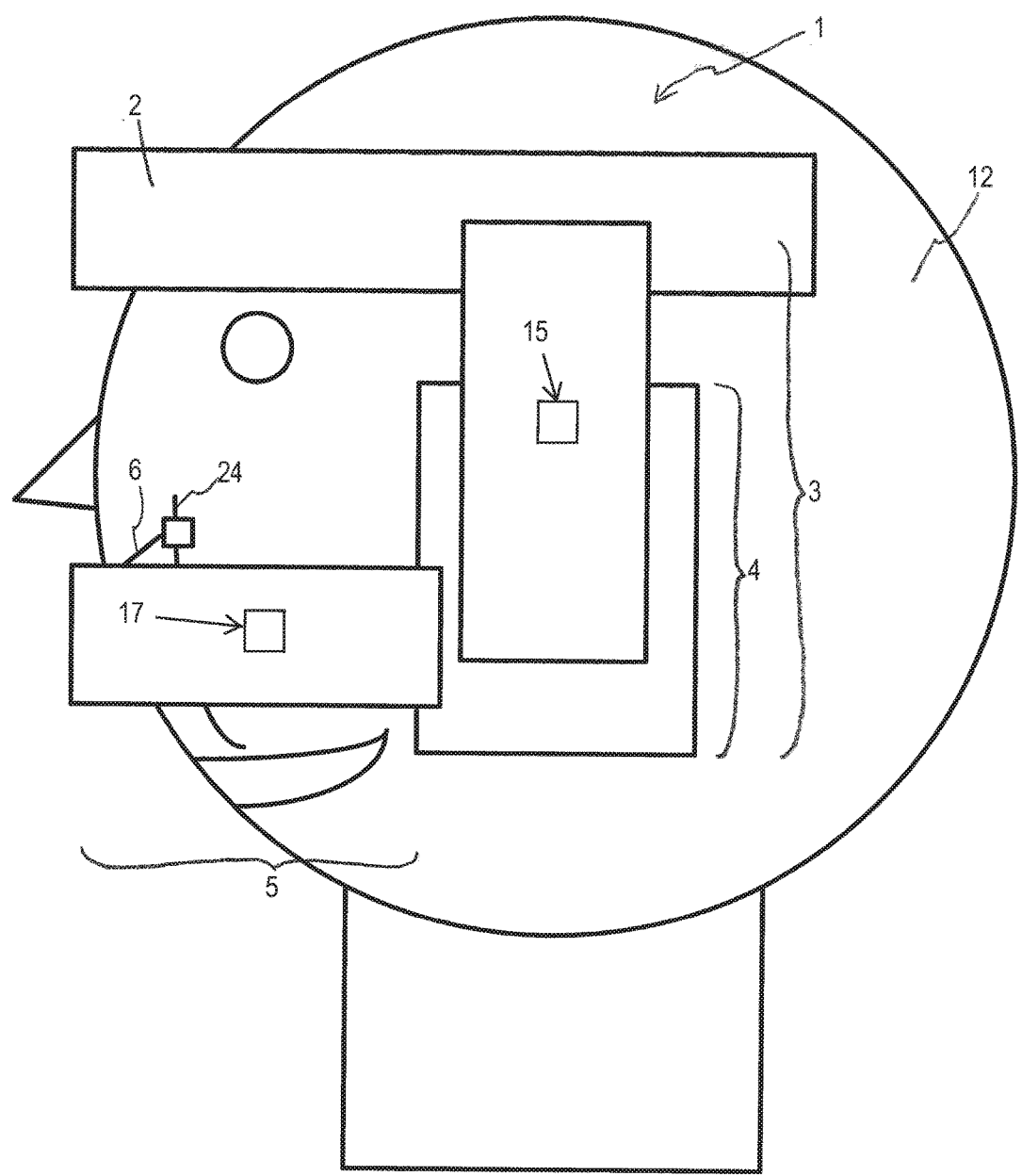
FIG. 1 depicts a representational illustration of an external distraction apparatus on the head of a patient.

FIG. 1 depicts a representational, side view illustration of an example external distraction apparatus 1 in accordance with an embodiment of the present disclosure. The external distraction apparatus 1 may be used to correct any number of craniofacial deformities through precise, multi-dimensional movement of a portion of the craniofacial skeleton in a prescribed direction over a prescribed magnitude (distraction vector). For example, depending upon the configuration, the external distraction apparatus 1 may perform distraction movements in 3 dimensions (i.e., 3 components of translation) with 3 axes of rotation (i.e., 3 components of rotation) to be moveable in 6 degrees of freedom. In some embodiments, the device may be configured to perform distraction movement in select degrees of freedom. The apparatus 1 may, for example, be used to correct various congenital craniofacial defects, trauma induced facial deformities, etc.

The external distraction apparatus 1 includes a stationary member or portion 2. The stationary member 2 may be fixed to the head of a patient 12. This may be accomplished through the use of standard fixation hardware such as fixation pins 20 (see, for example, FIG. 2). The stationary member 2 may serve to affix the external distraction apparatus 1 to the patient. The stationary member 2 may also serve as the frame of reference for all distraction movements performed by the apparatus 1. The stationary member 2 may be halo or horseshoe like in shape. A portion of the stationary member 2 may be anterior to the head of the patient 12 when the apparatus 1 is in place on the patient 12.

The apparatus 1 may include one or more moveable portions. In the example embodiment the apparatus 1 has a moveable portion including a number of movable units 3, 4, and 5. A moveable portion is a portion of the apparatus 1 that is moveable relative to the stationary member 2. As shown, the movable units 3, 4, and 5 may be disposed laterally (in relation to the patient 12). Such an arrangement ensures that the apparatus 1 is minimally obstructive to the patient 12 and provides easy access to the patient's 12 nose and mouth.

Only one side of the apparatus 1 is shown the sake of brevity, however, the opposite side of the apparatus 1 (not shown), likewise, may include a moveable portion and be divided into a number of moveable units. In the example embodiment, the apparatus 1 is symmetrical and the opposite side of the apparatus 1 is divided into corresponding, counterpart moveable units which mirror those of the shown side. Each of the movable units 3, 4, and 5 may be selectively displaced in order to generate distraction along a desired distraction vector. The moveable units 3, 4, and 5 may move in conjunction with or in relation to their counterpart moveable units on the opposite side of the apparatus 1. Additionally, one or more of the moveable units 3, 4, and 5 may form a sub-unit of a larger, parent movable unit. Such sub-units may move with and be included within their parent unit, but may also be moved relative to and independent of their parent unit, e.g., along another axis that the parent unit does not move along. This may allow for multidirectional distraction of the patient's 12 bone.

Each moveable unit 3, 4, 5 may be a collection of parts (or one part) which move(s) along or rotate(s) about a displacement axis or in a displacement direction. The displacement axes or directions may be chosen to maximize control over the distraction vector of the bone. Such a multi-axis capability allows precise, three dimensional movement of the bone being displaced. Consequentially, when the distraction process is finished, the facial bones and teeth may be very close to their targeted positions. This will help to eliminate the need for subsequent procedure, for example, to correct malocclusions.

Displacement of the moveable units 3, 4, 5 may be actuated in any suitable fashion. In some embodiments, the moveable units 3, 4, 5 may be manually actuated by a user. In other embodiments, actuation of the moveable units 3, 4, 5 may be automated. In some embodiments, at least one of the moveable units 3, 4, 5 may be manually actuated, and at least one other of the moveable units 3, 4, 5 may be actuated in an automated fashion.

Optionally, in some specific embodiments of the present disclosure, the apparatus 1 includes sensors 15, 17. The sensors 15, 17 may be used to measure displacement of the moveable units 3, 4, and/or 5. The sensors 15, 17 may be force sensors configured to measure the forces applied to the patient 12 (e.g., the portion of the patient that is being distracted). The sensors 15, 17 may be disposed or attached to any part of the apparatus 1, including but not limited to, the stationary member 2, the moveable units 3, 4, 5, a shaft or linear slide disposed therein, or other position to measure apparatus of the apparatus 1.

For example, the first sensor 15 may be integrated into a motor disposed therein while the second sensor 17 is disposed in another motor disposed within the moveable unit 4. The sensors 15, 17 may provide feedback to a processor (e.g., processor 532 or programmable logic device 534, described below with regard to FIG. 20). The processor (e.g., processor 532) may use the sensors 15, 17 in accordance with a predetermined force profile. The force profile may define a constant-force distraction vector, variable-force distraction vector, and/or variable distraction vector. The force profile may also define one or more torques that is applied to the portion of the patient 12 that is being distracted.

The force profile may also define a range of forces that are acceptable during a distraction. For example, the force profile may include upper and/or lower boundaries of force that should be applied to the portion of the patient 12 being distracted; this may be define when a predetermined schedule defines one or more velocity vectors of distraction. A processor (e.g., processor 532) may alarm if the force is not within the upper and lower boundaries. The upper and lower boundaries may be treatment-time dependent.

The apparatus 1 additionally includes coupling elements 6. Only one coupling element 6 is shown in the example view shown in FIG. 1. The other coupling element 6 is on the opposite, not shown side, of the apparatus 1. The coupling elements 6 may couple to transcutaneous rods 24 extending from retention plates (not shown) attached to a portion of the craniofacial skeleton. For example, the transcutaneous rod 24 may be anchored to a portion of the craniofacial skeleton, pass transmucosally into the mouth, and out between the lips of the patient 12, in some specific instances. The coupling elements 6 may be any suitable type of coupling element. It may be desirable that the coupling elements be of rigid construction or be substantially non-compliant. As shown, the coupling element 6 is coupled directly to the transcutaneous rods 24 in a fixed, and static manner such that the transcutaneous rod 24 and coupling element 6 are not capable of movement relative to one another. This embodiment obviates the need for an intermediary span of surgical wire. This embodiment also allows both linear forces as well as moment loads to be transferred across this coupling connection. This may help to ensure that the actual distraction vector is the same as the distraction vector commanded by the apparatus 1. Additionally, such a direct coupling is more durable when compared to a connection utilizing an intermediary span of surgical wire. However, in some embodiments, an intermediary span of surgical wire may be used. In some embodiments, the transcutaneous rods 24 may be any suitable standard hardware used in the art.

Since the transcutaneous rods 24 may be routed and bent to shape during the operation, the location of the extracorporeal portion of the transcutaneous rods 24 is not known and will vary from surgery to surgery. Therefore, it may be desirable that the coupling elements 6 be adjustable in order to ensure they may intercept and couple to the transcutaneous rods 24 regardless of the spatial orientation of the transcutaneous rods 24 post surgery.

Figure 2:
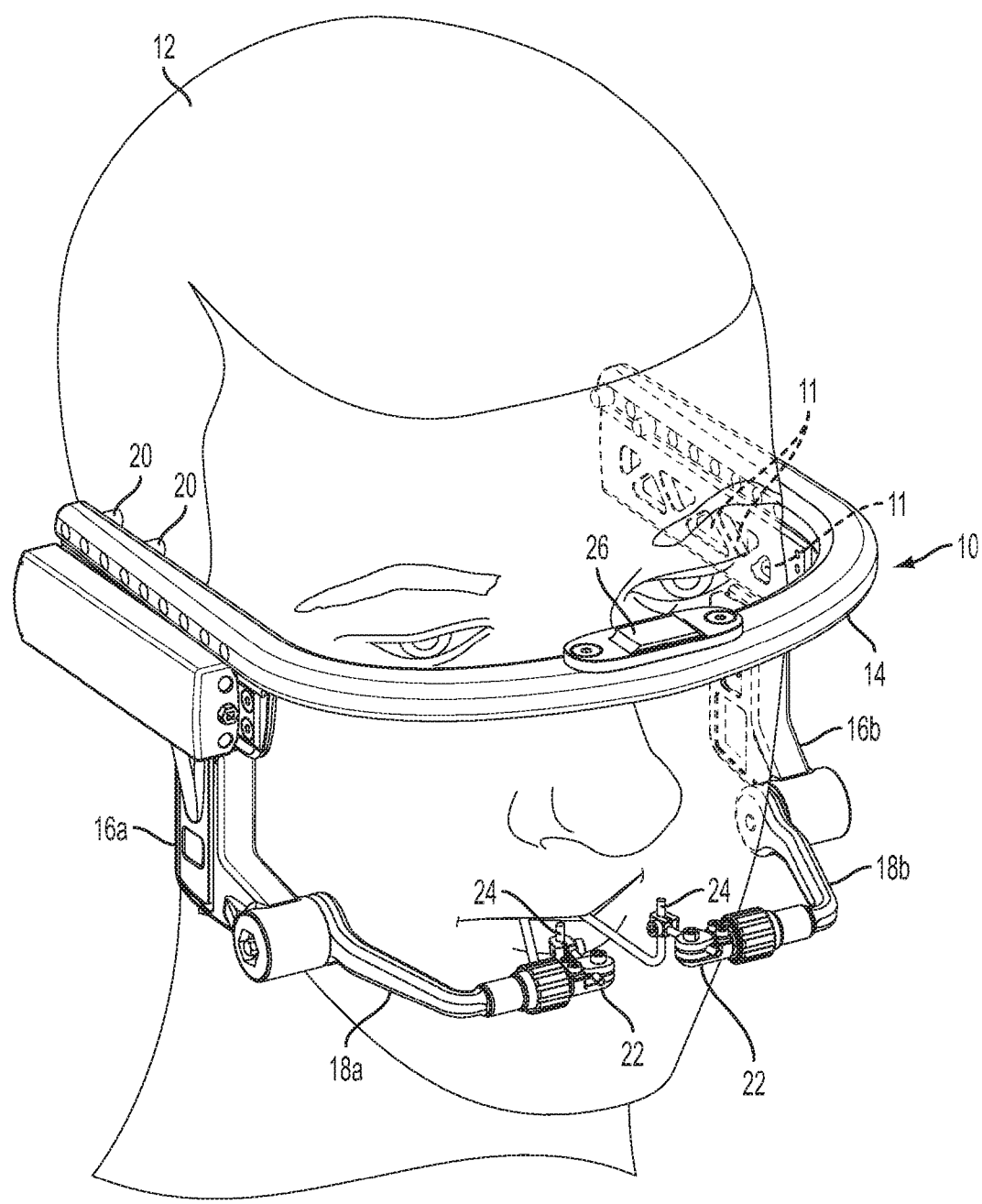
FIG. 2 depicts an perspective view of an example embodiment of an external distraction apparatus on the head of a patient.

FIG. 2 depicts an example embodiment of an external distraction apparatus 10 in place on the head of a patient 12. The external distraction apparatus 10 may be used to correct any number of craniofacial deformities through precise, multi-dimensional movement of a portion of the craniofacial skeleton in a prescribed direction over a prescribed magnitude (distraction vector). The apparatus 10 may, for example, be used to correct various congenital craniofacial defects, trauma induced facial deformities, etc.

The apparatus 10 may be made of any of a variety of suitable materials. It may be desirable that the materials chosen are lightweight, but possess a high elastic modulus. In some specific embodiments, magnesium may be used. In other specific embodiments, aluminum, titanium, an aluminum alloy, a titanium alloy, or some combination thereof may be used. In some specific embodiments, a material (e.g., a low density material) may be used that facilitates medical imaging (e.g., MRI, CT, fluoroscopy, etc.) of the patient 12 while the apparatus 10 is attached to the patient 12. Additionally, it may be desirable that the apparatus 10 is made from materials which may be autoclaved without degrading. For example, it may be desirable for any plastic components of the apparatus 10 to be made from high temperature plastics. Also, in some embodiments, non-essential material or non-structural portions of material may be removed from the apparatus 10 to lighten the apparatus 10. As shown in FIG. 2, a number of cut-outs 11 are included to lighten the apparatus 10.

The example apparatus 10 in FIG. 2 includes a stationary member or halo portion 14. The halo portion 14 may be a single continuous piece of material. The halo portion 14 may be offset from and wrap around the head of the patient 12. The halo portion 14 in the example embodiment wraps around the head of the patient 12 such that a portion of the halo portion 14 is anterior to the head of the patient 12.

The apparatus 10 in FIG. 2 also includes two upright bodies 16a, b which may extend inferiorly from the halo portion 14. The upright bodies 16a, b are disposed laterally in the example embodiment in FIG. 2. Extending medially from the inferior end each of the upright bodies 16a, b are arm members 18a, b. The upright bodies 16a, b and attached arm members 18a, b may be moved in relation to the halo portion 14 to cause distraction of a portion of the craniofacial skeleton along a desired distraction vector.

The halo portion 14 of the apparatus 10 may be anchored to the patient 12 via a number of pins 20. These pins 20 serve to render the halo portion 14 stationary with respect to the superior, lateral portions of the skull. In the depicted embodiment, only two pins 20 are shown; however, any suitable number of pins 20 may be used in other embodiments or depending on the needs of the patient 12. The pins 20 used may be any suitable fixation pin used in the art. Also as shown, the halo portion 14 includes a number of holes through which the fixation pins 20 may be inserted. Thus pins 20 may be spaced apart from each other differing amounts depending on the holes selected. This may help allow a user to optimally secure the apparatus 10 such potential for drift or movement is minimized.

The apparatus 10 additionally includes two coupling elements 22 which are disposed at the medial ends of the arm members 18a, b. These coupling elements 22 may couple to transcutaneous rods 24 extending from retention plates (not shown) attached to a portion of the craniofacial skeleton. In the example embodiment, the coupling elements 22 are clamps which clamp around the transcutaneous rods 24 creating an attachment point between the apparatus 10 and the transcutaneous rods 24. As shown, the coupling elements 22 are rigid and coupled directly to the transcutaneous rods 24 in a fixed, and static manner such that the transcutaneous rods 24 and coupling elements 22 are not capable of movement relative to one another. This may help to ensure that the actual distraction vector is the same as the distraction vector commanded by the apparatus 10. It may also allow both linear and moment forces to be transmitted through the coupling elements 22.

In other embodiments, the coupling elements 22 may include an eyelet or the like for a connecting wire extending from the transcutaneous rod 24 to the coupling element 22. In some instance or for some procedures, the coupling elements 22 may couple to an intraoral splint. Additionally, the coupling elements 22 are adjustable in the example embodiment. Adjustment of the coupling elements 22 will be further described later in the specification.

Also shown in FIG. 2 is an adapter 26. The adapter 26 may allow for a vertical bar (not shown) to be attached to the apparatus 10. Thus, the adapter 26 may function as a fail-safe which allows a user to convert the apparatus 10 into an external distractor which uses a vertical bar running down the midline of the face of the patient 12 if necessary. Distraction may then be performed via distraction screws on a cross-bar which are directly or indirectly connected to respective transcutaneous rods 24. The adapter 26 may be any suitable adapter. In the example embodiment, the adapter 26 includes a dove-tail feature which may matingly engage a cooperating feature attached to the vertical bar. The adapter 26 may also accommodate various fasteners (not shown) which may fixedly couple a vertical rod in place on the halo portion 14 of the external distraction apparatus 10.

Figure 3:
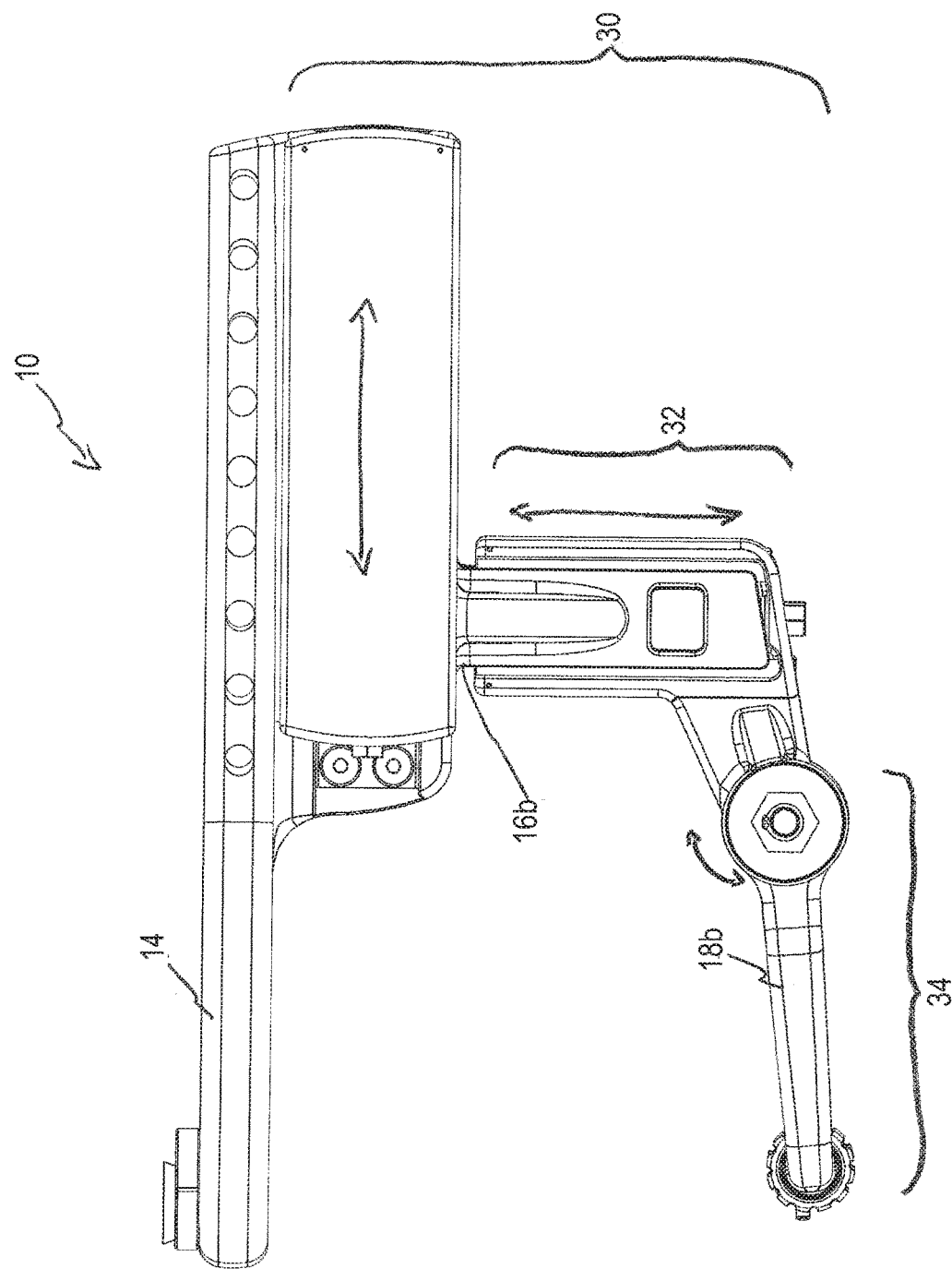
FIG. 3 depicts a side view of an example embodiment of an external distraction apparatus.

FIG. 3 depicts a side view of the example external distraction apparatus 10 shown in FIG. 2. As shown, the lateral, side portions of the apparatus 10 may be divided into a number of movable units 30, 32, and 34. Only one side of the apparatus 10 is shown the sake of brevity, however, the opposite side of the apparatus 10 (not shown), likewise, may be divided into a number of moveable units. In the example embodiment, the apparatus 10 is symmetrical and the opposite side of the apparatus 10 is divided into corresponding, counterpart moveable units which mirror those of the shown side. Each of the movable units 30, 32, and 34 may be selectively displaced in order to generate distraction along a desired distraction vector. The moveable units 30, 32, and 34 may move in conjunction with or in relation to their counterpart moveable units on the opposite side of the apparatus 10. Additionally, one or more of the moveable units 30, 32, and 34 may form a sub-unit of a larger movable unit.

In the exemplary embodiment shown, the first moveable unit 30 includes the entire upright body 16b and arm member 18b. The second moveable unit 32 and third moveable unit 34 are sub-units of the first moveable unit 30. The entirety of the first moveable unit 30 may be selectively displaced in relation to the stationary halo portion 14 of the apparatus 10 along a first displacement direction or axis. In the example embodiment, the first displacement axis extends in roughly posterior to anterior direction. Since the second moveable unit 32 and third moveable unit 34 are sub-units of the first moveable unit 30, displacement of the first moveable unit 30 also causes displacement of the second moveable unit 32 and third moveable unit 34 along the first displacement axis.

The second moveable unit 32 in the example embodiment includes an inferior portion of the upright body 16b and the entire arm member 18b. Additionally, the third moveable unit 34 is a sub-unit of the second moveable unit 32. The entirety of the second moveable unit 32 may be displaced in relation to the halo portion 14 of the apparatus 10 and the remaining portion of the first moveable unit 30. The second moveable unit 32 may be displaced along a second displacement direction or axis. The second displacement axis may be substantially perpendicular to the first displacement axis. With respect to the page, the second displacement axis is roughly vertical. Since the third moveable unit 34 is a sub-unit of the second moveable unit 32, displacement of the second moveable unit 32 also causes displacement of the third moveable unit 34 along the second displacement axis.

The third moveable unit 34 in the example embodiment includes the arm member 18b. The entirety of the third moveable unit 34 may be displaced in relation to the halo portion 14 of the apparatus 10 and the remaining portions of the first and second moveable unit 30, 32. The third moveable unit 34 may be displaced about a pitch axis. The pitch axis may be perpendicular to both the first displacement direction and second displacement direction. With respect to the page, the pitch axis extends toward the back of the page.

The moveable units 30, 32, and 34 may be displaced using any suitable means. In some embodiments, the moveable units 30, 32, and 34 may be displaced by a user via manual actuation. In such embodiments, a user may interface with a jack screw, rack and pinion, or other displacement mechanism to effect displacement of a desired moveable unit. In some embodiments, one or more of the moveable units 30, 32, and 34 may be displaced in an automated manner. For example, some embodiments may include one or more motors and control electronics to displace a desired moveable unit. In some embodiments all of the moveable units 30, 32, and 34 may be displaced in an automated manner. In embodiments where one or more of the moveable units 30, 32, and 34 is displaced in an automated manner, there may be a manual override for each such moveable unit 30, 32, and 34. Other displacement means may also be used.

Figure 4:
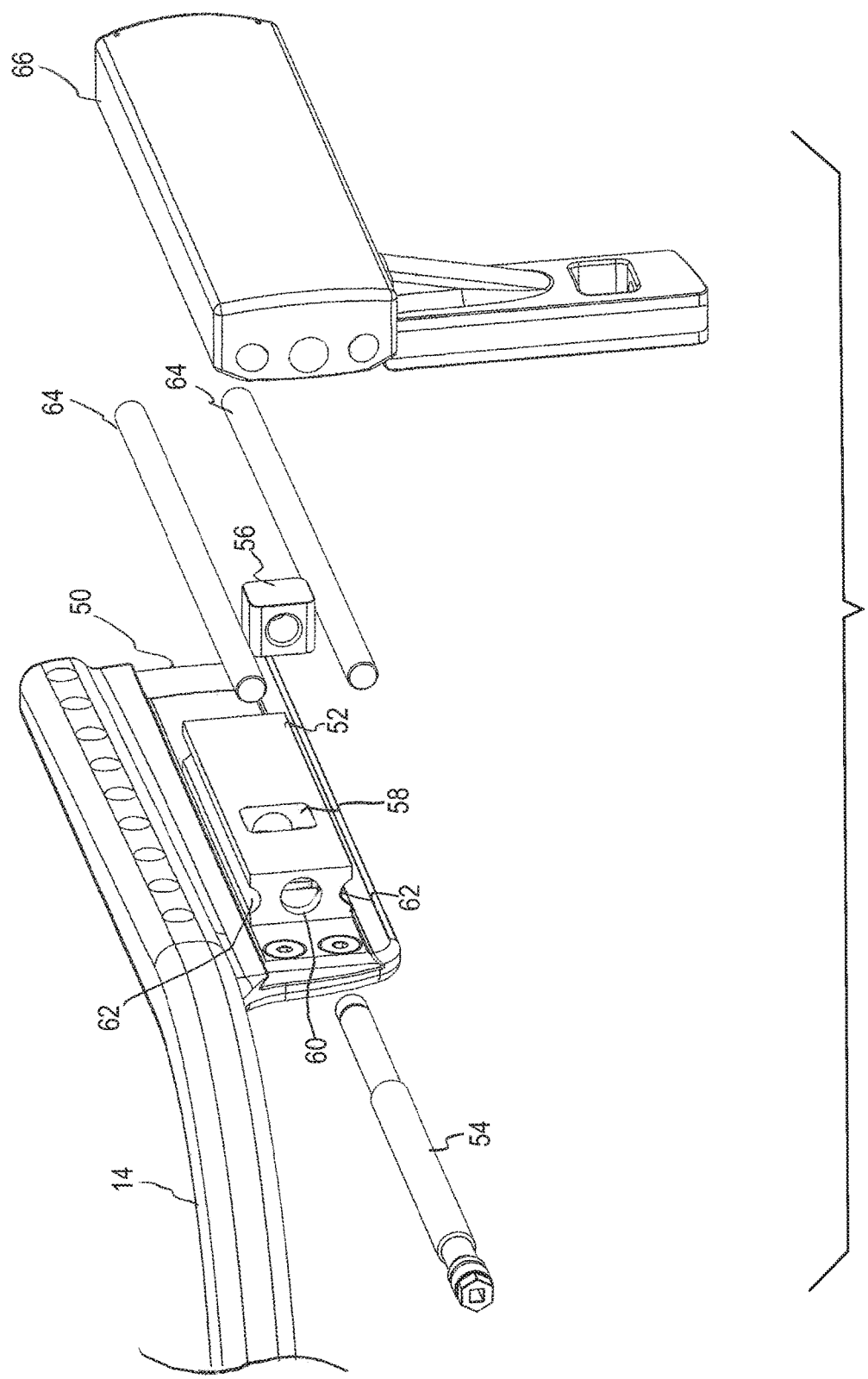
FIG. 4 depicts an exploded view of example actuation components for a moveable unit of the example external distraction apparatus shown in FIG. 3.

FIG. 4 depicts an exploded view of example actuation components for the first moveable unit 30 (see, for example, FIG. 3). As shown, the example actuation components are configured to allow for manual actuation. In alternate embodiments, non-manual actuation components may be used. As shown, a stationary block 50 projects inferiorly from the halo portion 14 of the external distraction apparatus. Included on the stationary block 50 is a receiving structure 52 for a jackscrew 54 and nut 56. As shown, the nut 56 may be placed into and retained within a void 58 on the receiving structure 52. A pass-through 60 may extend through the receiving structure 52 to allow the jackscrew 54 to be fed through the receiving structure 52 and nut 56. The receiving structure 52 additionally includes bearing surfaces 62 for a respective number of bearing shafts 64.

Figure 5:
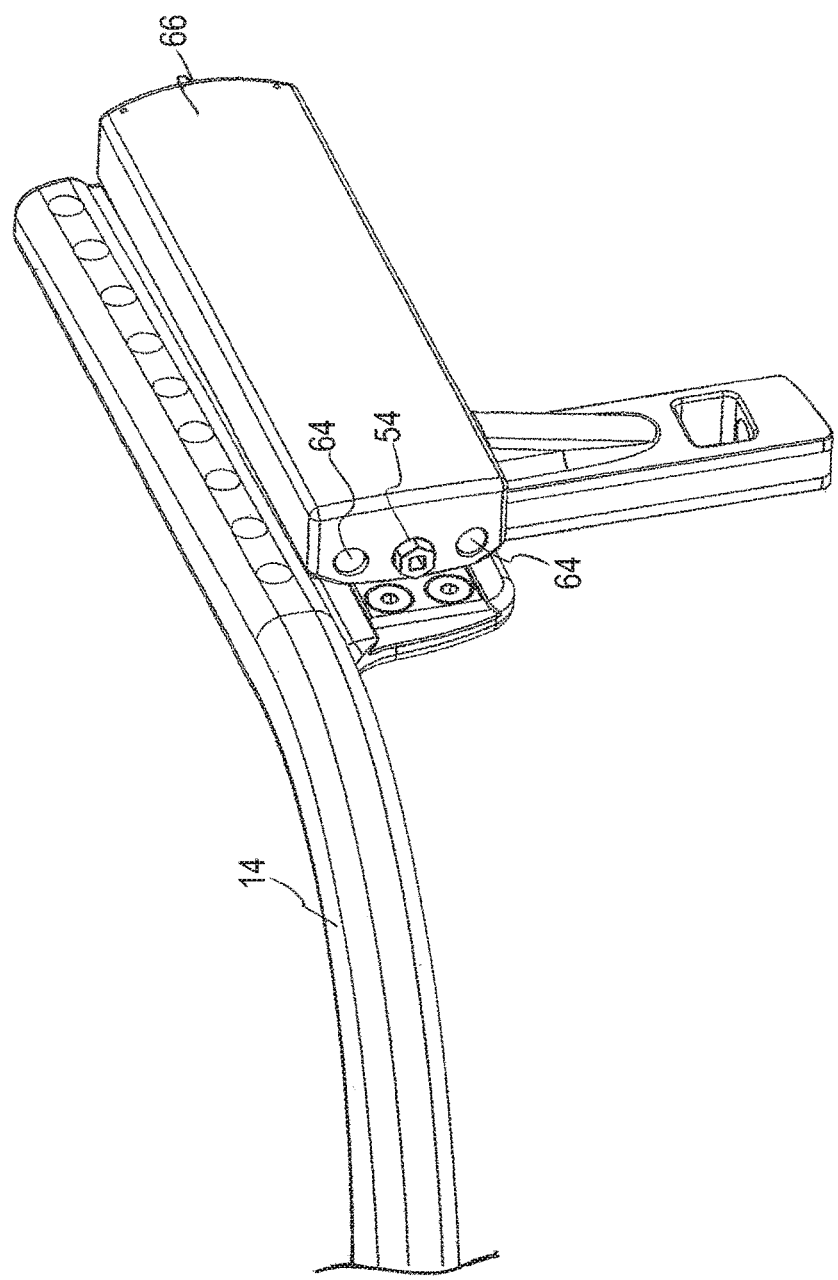
FIG. 5 depicts an assembled view of the example actuation components shown in FIG. 4.

When fully assembled (refer now also to FIG. 5), a superior housing 66 may be placed over the receiving structure 52. The bearing shafts 64 may be fixedly held within the superior housing 66. The head of the jackscrew 54 may also project out of the superior housing 66 when fully assembled. The jackscrew 54 may be prevented from displacing axially with respect to the superior housing 66. This may be accomplished through the use of one or more C-clip(S) or the like (not shown). With the use of a suitable screwdriver/wrench (not shown), the user may rotate the jackscrew 54 to cause it to advance into or retreat out of the nut 56 retained within the receiving structure 52. Such movement will consequently cause the superior housing 66 to displace in the first displacement direction as described above.

Figure 6:
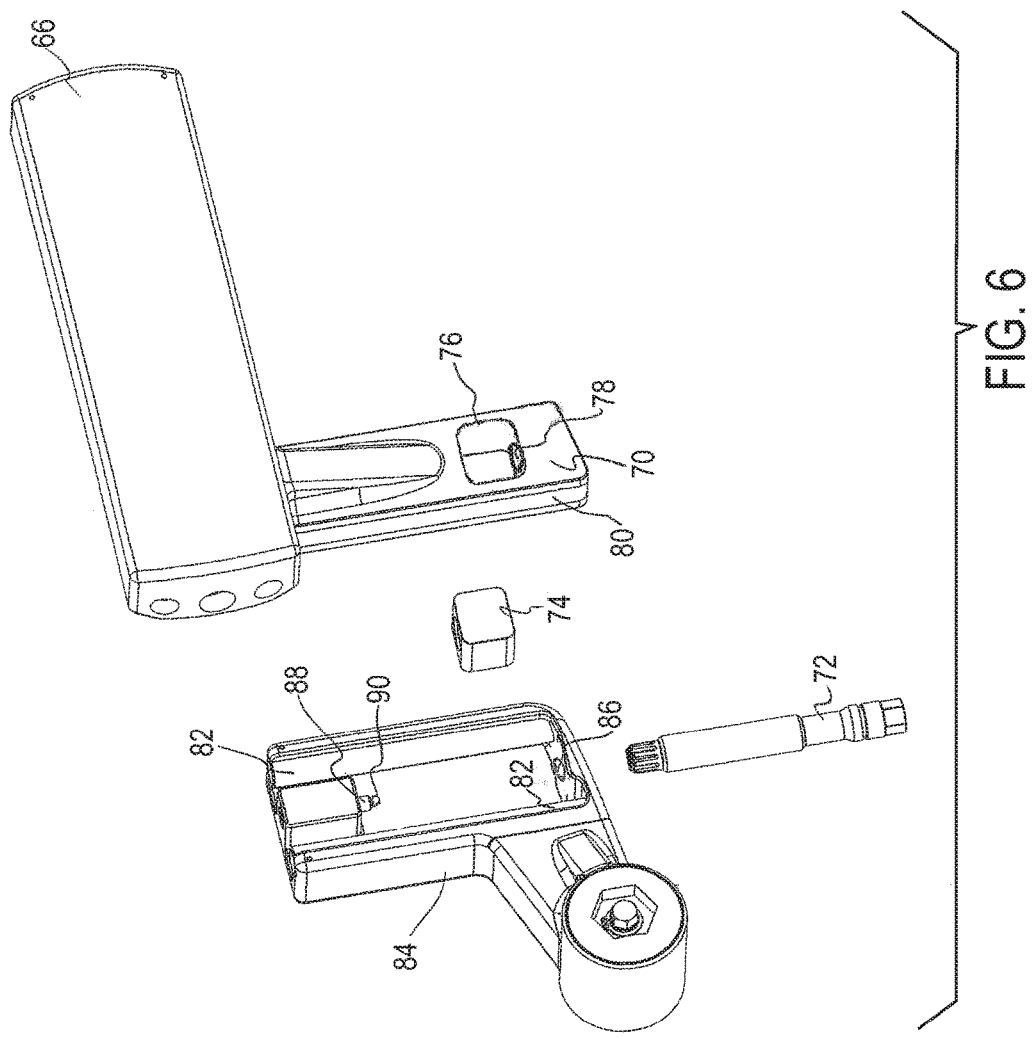
FIG. 6 depicts an exploded view of example actuation components for a moveable unit of the example external distraction apparatus shown in FIG. 3.

FIG. 6 depicts an exploded view of example actuation components for the second moveable unit 32 (see, for example, FIG. 3). As shown, the example actuation components are configured to allow for manual actuation. In alternate embodiments, non-manual actuation components may be used. As shown, the superior housing 66 shown above in relation to FIG. 4 is also depicted in FIG. 6. The superior housing 66 includes a receiving structure 70 for a jackscrew 72 and a nut 74. As shown, the nut 74 may be placed into and retained within a void 76 on the receiving structure 70. A pass-through 78 may extend through the receiving structure 70 to allow the jackscrew 72 to be fed through the receiving structure 70 and nut 74. The receiving structure 70 additionally includes bearing surfaces 80 for a respective number of bearing shafts 82.

Figure 7:
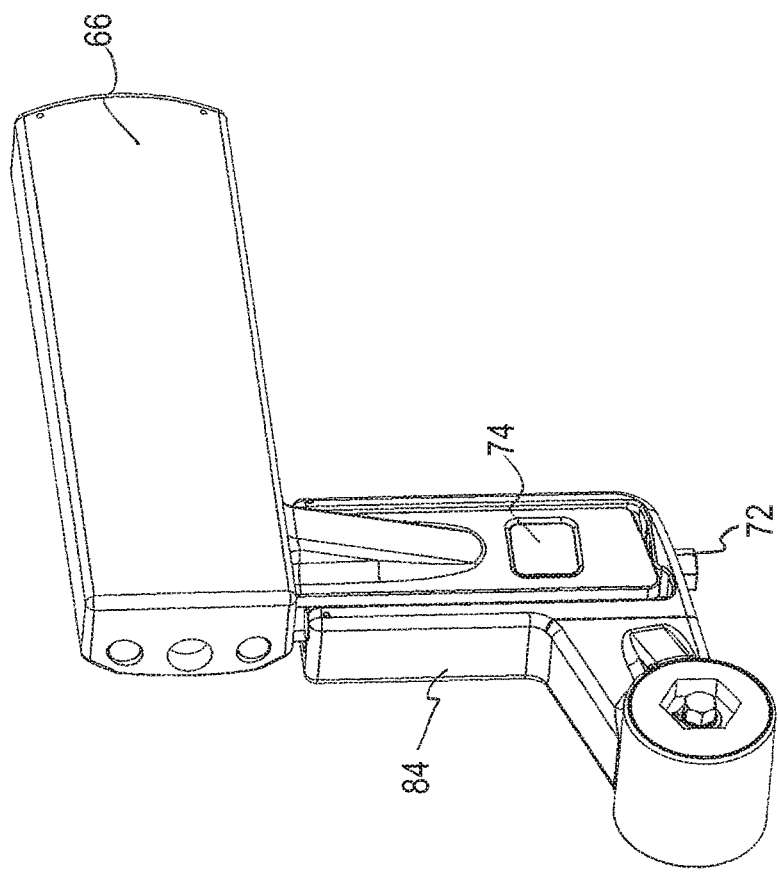
FIG. 7 depicts an assembled view of the example actuation components shown in FIG. 6.

An example inferior housing 84 is also shown in FIG. 6. The inferior housing 84 includes a recess which is sized to accept the portion of the superior housing 66 including the receiving structure 70. A pass through 86 is included in the inferior housing 84 which allows the jackscrew 72 to be inserted through the inferior housing 84 and into the receiving structure 70 when fully assembled (refer now also to FIG. 7). As shown, a set screw 88 is also included as part of the inferior housing 84. In the example embodiment, the set screw 88 includes a cup in which a ball bearing 90 is disposed.

When fully assembled (refer now also to FIG. 7), the superior housing 66 may be placed into the recess on the inferior housing 84. The bearing shafts 82 may be fixedly held within the inferior housing 84. The head of the jackscrew 72 may also project out of the inferior housing 84 when fully assembled. The jackscrew 72 may be prevented from displacing axially with respect to the inferior housing 84. This may be accomplished through the use of one or more C-clip or the like (not shown). Additionally, an end of the jackscrew 72 may include a cup-like feature which allows it to mate with the ball bearing 90. With the use of a suitable screwdriver/wrench (not shown), the user may rotate the jackscrew 72. Such rotation will cause the nut 74 to advance or retreat along the length of the jackscrew 72. Since the nut 74 is retained within the receiving structure 70, such movement of the nut 74 will consequently cause the inferior housing 84 to displace in the second displacement direction as described above.

Figure 8:
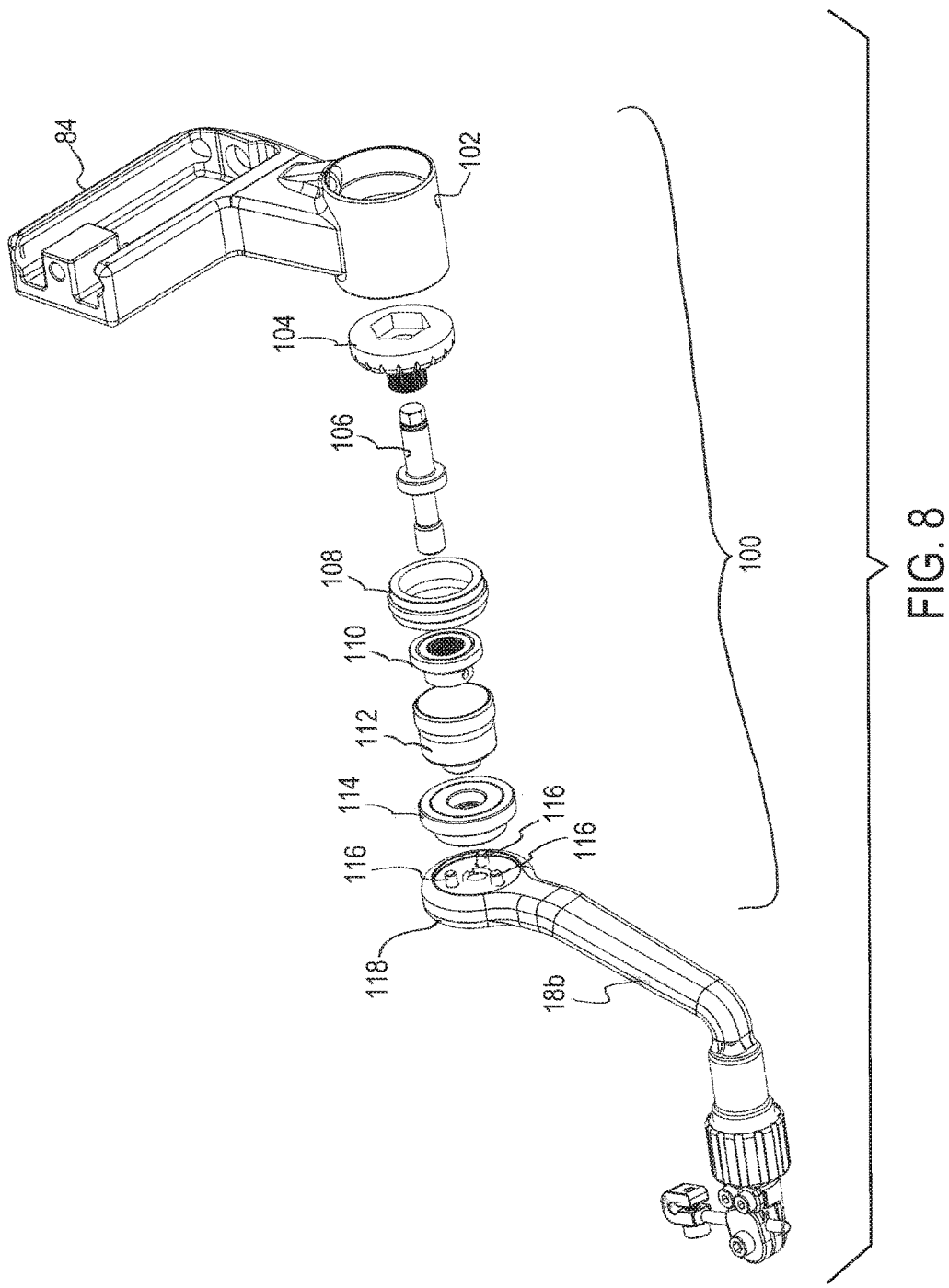
FIG. 8 depicts an exploded view of example actuation components for a moveable unit of the example external distraction apparatus shown in FIG. 3.

FIG. 8 depicts an exploded view of example actuation components for the third moveable unit 34 (see, for example, FIG. 3). As shown, the example actuation components are configured to allow for manual actuation. In alternate embodiments, non-manual actuation components may be used. As shown, the actuation components in FIG. 4 are components of a harmonic drive assembly 100. It may be desirable to use a harmonic drive for actuation of the third moveable unit 34 due to the large gear reductions which may be afforded by such an arrangement. In alternate embodiments, a harmonic drive need not necessarily be used. In embodiments using a harmonic drive assembly 100, any suitable harmonic drive assembly which generates any suitable gear reduction may be used.

Figure 9:
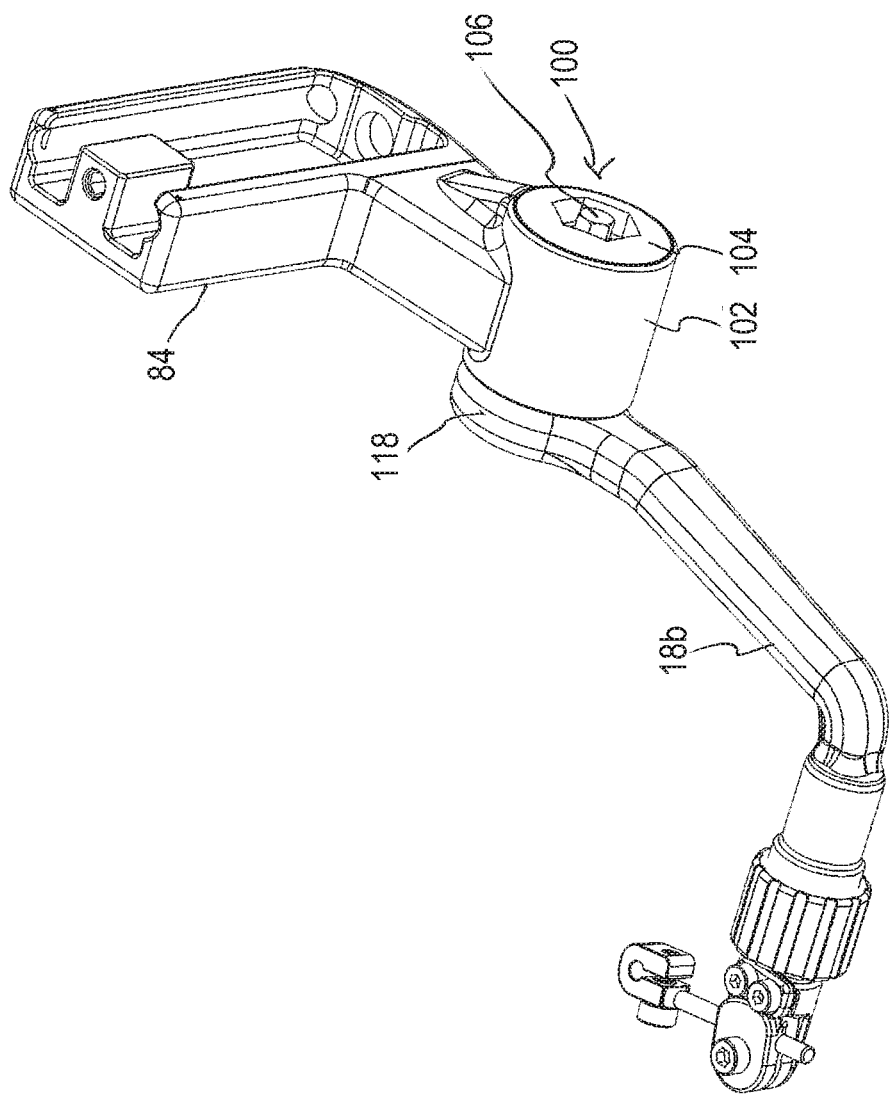
FIG. 9 depicts an assembled view of the example actuation components shown in FIG. 8.

In the example embodiment, the harmonic drive assembly 100, when assembled (refer now also to FIG. 9), may be enclosed with in a sleeve 102 included in the inferior housing 84. The harmonic drive assembly 100 includes an input head 104 and bolt 106 through which a user may manually provide a rotational input to the harmonic drive assembly 100 by means of a suitable screwdriver/wrench (not shown). A circular spline 108, wave generator 110, and flex spline 112 are also included. Rotation may be delivered through these components to a drive output 114. The drive output 114 may couple to an attachment feature 118 on the arm member 18b by any suitable means. As shown the drive output 114 couples to the attachment feature 118 via a number of dowel pins 116. Thus, the third moveable unit 34 (see FIG. 3) may be compelled rotate about its pitch axis (as described above) as a result of rotational input at the input head 104.

Figure 10:
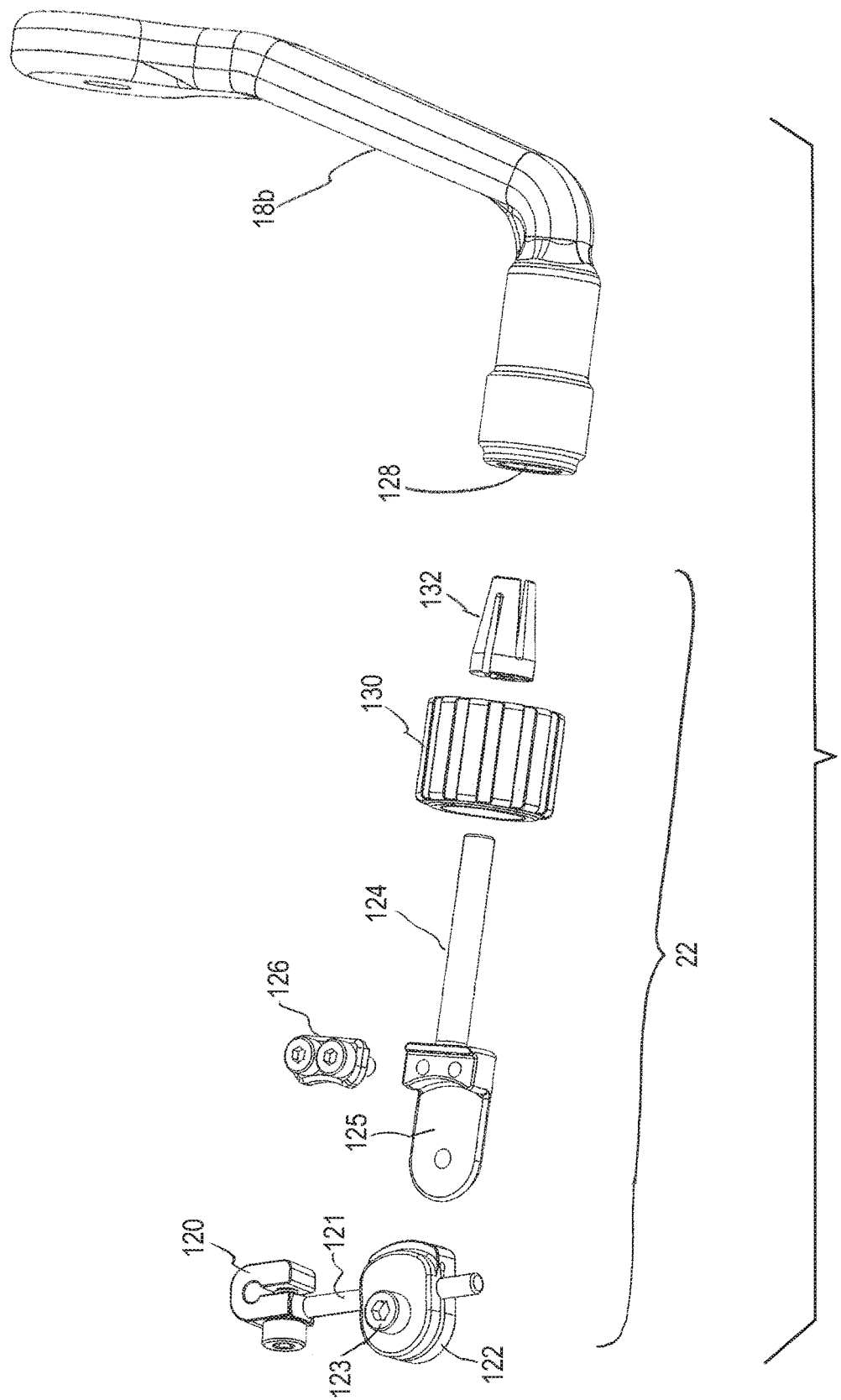
FIG. 10 depicts an exploded view of an example coupling element which may be included in an external distraction apparatus.
Figure 11:
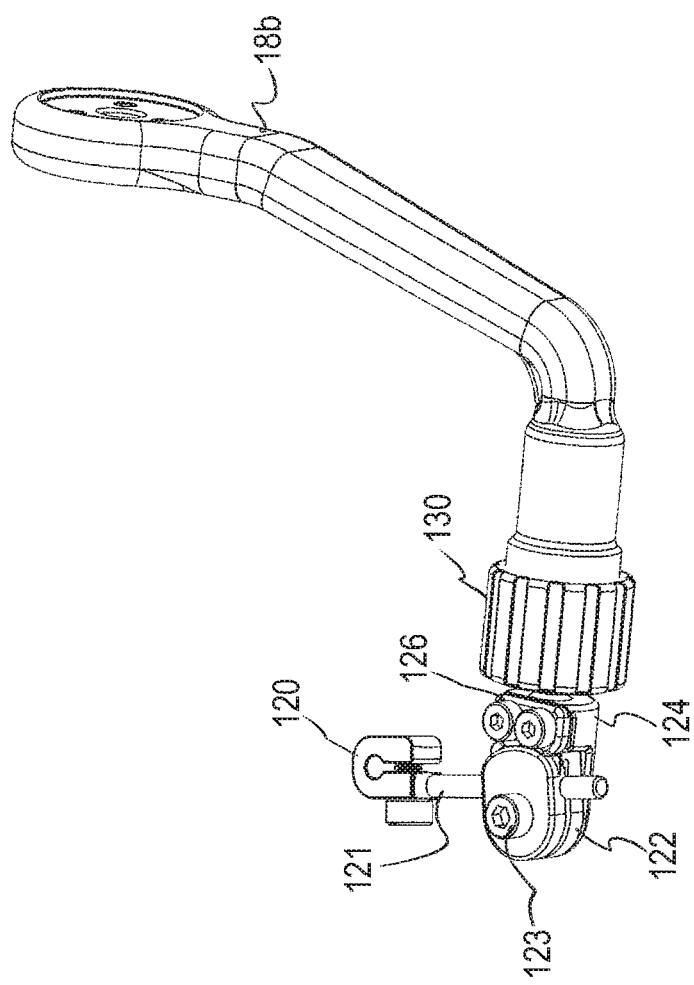
FIG. 11 depicts an assembled view of the example coupling element shown in FIG. 10.

FIG. 10 depicts an exploded view of an example coupling element 22 and arm member 18b. An assembled view of the coupling element 22 and arm member 18b is shown in FIG. 11. As mentioned above, the coupling element 22 may be used to couple to a transcutaneous rod 24 (see FIG. 2) extending from a retention plate (not shown) attached to a portion of the craniofacial skeleton. The example coupling element 22 is the same as that shown and described in relation to FIG. 2.

As mentioned above in relation to FIG. 2, ensuring that a coupling element 22 is adjustable may be desirable. The coupling element 22 depicted in FIGS. 10 & 11 is configured to allow for a number of adjustments. These adjustments may allow the coupling element 22 to couple to a transcutaneous rod 24 (see, FIG. 2) whose extracorporeal portion may be in a wide range of spatial orientations.

As shown, the coupling element 22 includes a clamp 120. The clamp 120 may statically couple to a transcutaneous rod 24 (see FIG. 2). The clamp 120 is attached to a boom 121. The boom 121, in turn, is held static by a boom clamp 122. When the boom clamp 122 is not clamping the boom 121, the boom 121 is free to displace axially and rotate about its longitudinal axis. Once in the proper orientation, the boom clamp 122 may be used to clamp the boom 121 in that orientation.

The coupling element 22 additionally includes boom clamp mount 124. The boom clamp mount 124 includes a seating surface 125 on which the boom clamp 122 may be placed. A boom clamp screw 123 may be used to pivotally couple the boom clamp 122 to the seating surface 125. Tightening the boom clamp screw 123 may also cause the boom clamp to clamp down on the boom 121. The boom clamp 122 may be rotated about the axis of the boom clamp screw 123 until the boom clamp 122 and its attached components are in a desired orientation. A clasping member 126 may then be introduced to keep the boom clamp 122 and its attached components in the desired orientation.

The boom clamp mount 124 may be placed into a socket 128 in the arm member 18b. A chuck 130 may be included to secure the boom clamp mount 124 within the socket 128. Additionally, such a chuck 130 may allow the boom clamp mount 124 to be rotated about the axis of the socket 128 and displaced axially with regard to the socket 128 until the boom clamp mount 124 is in a desired orientation. In the example embodiment, the chuck 130 acts on a collet 132 to secure the boom clamp mount 124 within the socket 128 in the desired orientation. In other embodiments, any other suitable variety of chuck arrangements may be used.

In some embodiments, a portion of the coupling element 22 may include a compliant region, a spring element, etc. Such a region may help to smooth any forces applied to distract the bone. Such an arrangement may be particularly desirable in embodiments where the external distraction apparatus is used to perform intermittent distraction of the bone (e.g. once or a few time a day). In some embodiments, the compliant region or spring element may be included in the boom 121, for example.

Figure 12:
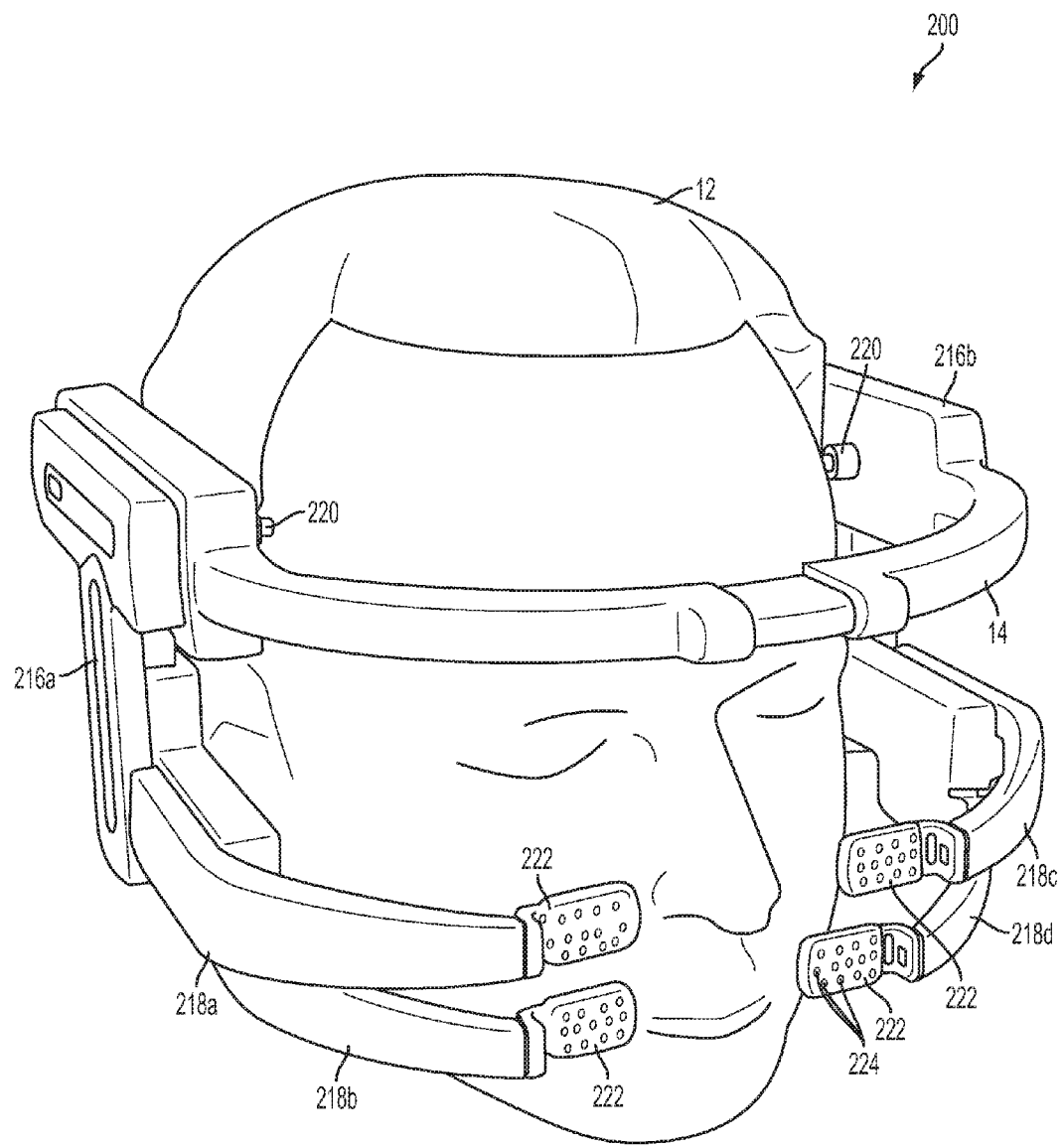
FIG. 12 depicts a perspective view of an example embodiment of an external distraction apparatus on the head of a patient.

FIG. 12 depicts a perspective view of an example embodiment of an external distraction apparatus 200 in place on the head of a patient 12. Like the, external distraction apparatus 10 shown in FIG. 2, the external distraction apparatus 200 in FIG. 12 may be used to correct any number of craniofacial deformities through precise, three dimensional movement of a portion of the craniofacial skeleton in prescribed direction over a prescribed magnitude (distraction vector).

The apparatus 200 may be made of any of a variety of suitable materials. It may be desirable that the materials chosen are lightweight, but possess a high elastic modulus. In some embodiments, non-essential material or non-structural portions of material may be removed from the apparatus 200 to lighten the apparatus 200. Additionally, it may be desirable that the apparatus 200 is made from materials which may be autoclaved without degrading.

The example apparatus 200 in FIG. 12 includes a halo portion 214. The device also includes two upright bodies 216a, b which may extend inferiorly from the halo portion 214. The upright bodies 216a, b are disposed laterally in the example embodiment shown in FIG. 12. Extending medially from the inferior end each of the upright bodies 216a, b are arm members 218a-d. The upright bodies 216a, b and attached arm members 218a-d may be moved in relation to the halo portion 14 to cause distraction of a portion of the patient's 12 craniofacial skeleton along a desired distraction vector.

The halo portion 214 of the apparatus 200 may be anchored to the patient 12 via a number of pins 220. These pins 220 serve to render the halo portion 214 stationary with respect to the superior, lateral portions of the skull. Any suitable number of pins 220 may be used depending on the needs of the patient 12. In the depicted embodiment, only two pins 220 are visible. The pins 220 used may be any suitable fixation pin used in the art.

Still referring to FIG. 12, the apparatus 200 may include an adapter 226. The adapter 226 is similar to the adapter 26 shown and described in relation to FIG. 2. As above, the adapter 226 may allow for a vertical bar (not shown) to be attached to the apparatus 200. Thus, the adapter 226 may function as a fail-safe which allows a user to convert the apparatus 10 into an external distractor which uses a vertical bar running down the midline of the face of the patient 12 if necessary.

The apparatus 200 additionally includes coupling elements 222 which are disposed at the medial ends of the arm members 218a-d. These coupling elements 222 may couple to transcutaneous rods 24 extending from retention plates (not shown) attached to a portion of the craniofacial skeleton. The coupling elements 222 may be any suitable type of coupling element. It may be desirable that the coupling elements 222 are coupled to the transcutaneous rods 24 in a fixed, and static manner such that the transcutaneous rods 24 and coupling elements 222 are not capable of movement relative to one another. This may help to ensure that the actual distraction vector is the same as the distraction vector commanded by the apparatus 200. In some embodiments, the coupling elements 222 may connect to the transcutaneous rods 24 via a linkage. The coupling elements 222 may also connect to wire segments. Such wire segments may extend from transcutaneous rods 24 to the coupling elements 222. In some instances, the wire segment may itself be transcutaneous and anchor to a portion of the craniofacial skeleton by means of a retention plate. Alternatively, the coupling elements 222 may couple to an intraoral splint.

The coupling elements 222 may be configured to be adjustable in some embodiments. For example, in some embodiments, the coupling elements 222 on the external distraction apparatus 200 may be similar to those shown and described in relation to FIG. 10-11 or FIGS. 26-30. Alternatively, and as shown in FIG. 12 the coupling elements 222 may be configured to have a number of coupling points 224 disposed in different locations on the coupling elements 222. Thus, any variance in the post surgery location of a transcutaneous rod 24 may be more easily accommodated for. The transcutaneous rod 24 may be coupled via a bracket or other suitable fastener which, for example, screws into the appropriate coupling points 224.

Figure 13:
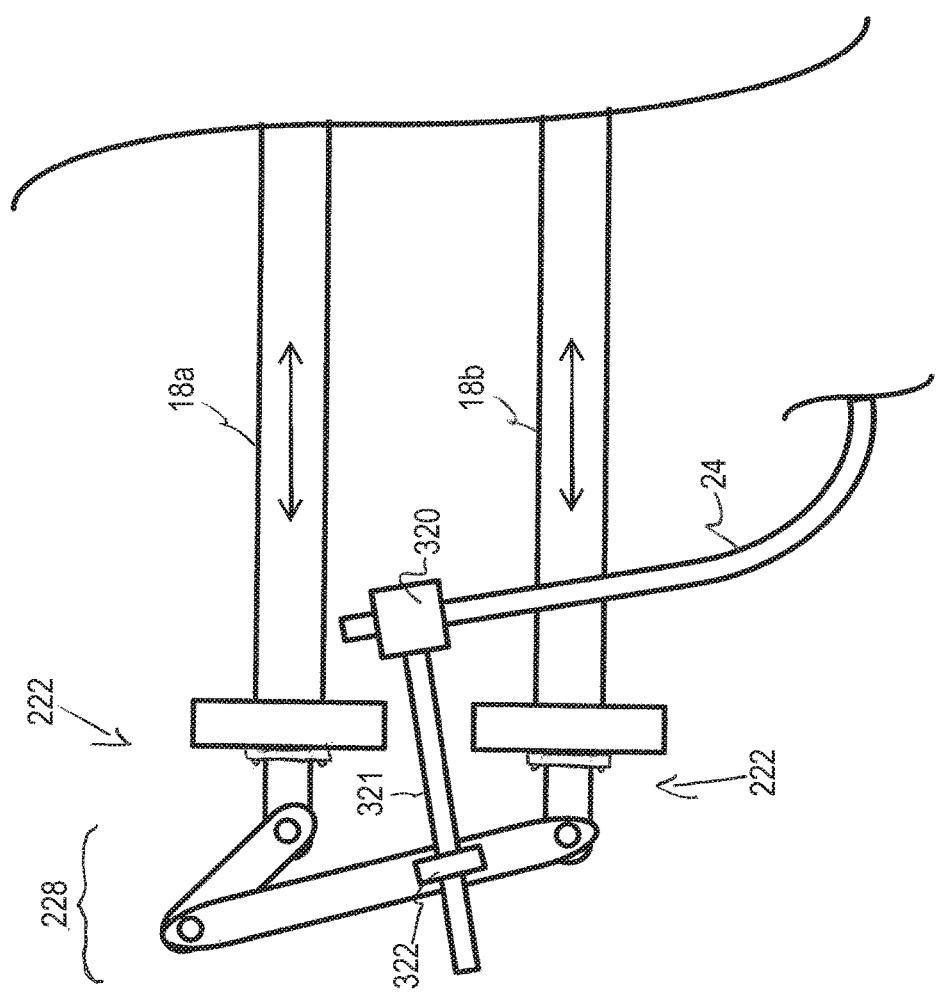
FIG. 13 depicts a representational illustration of a coupling element which may be included in an external distraction apparatus.

FIG. 13 conceptually depicts an alternative arrangement for a coupling element 222 which may be used on an external distraction apparatus such as that the external distraction apparatus 200 shown in FIG. 12. As shown, only the coupling elements 222 associated with arm members 218a, b are depicted in FIG. 13. The coupling elements 222 are conjoined by a linkage assembly 228. The linkage assembly 228 may couple to the coupling elements 222 via any suitable coupling points 224 (see FIG. 12) on the coupling elements 222. A boom 321 may extend from the linkage assembly 228 to a transcutaneous rod 24. The boom 321 may include a clamp 320 which fixedly and statically attaches the boom 321 to the transcutaneous rod 24. The boom 321, in turn, is held static by a boom clamp 322 on the linkage assembly 228. When the boom clamp 322 is not clamping the boom 321, the boom 321 is free to displace axially and rotate about its longitudinal axis. Once in the proper orientation, the boom clamp 322 may be used to clamp the boom 321 in that orientation.

As indicated, the arm members 218a, b may be selectively displaced in parallel with one another. Such an arrangement allows distraction to be effected from two linear joints which may or may not be moving at different rates. This may be desirable because it would allow a user to pitch about a non-fixed pitch axis or center of rotation. Such an arrangement may, however, add weight and complexity to the apparatus.

Figure 14:
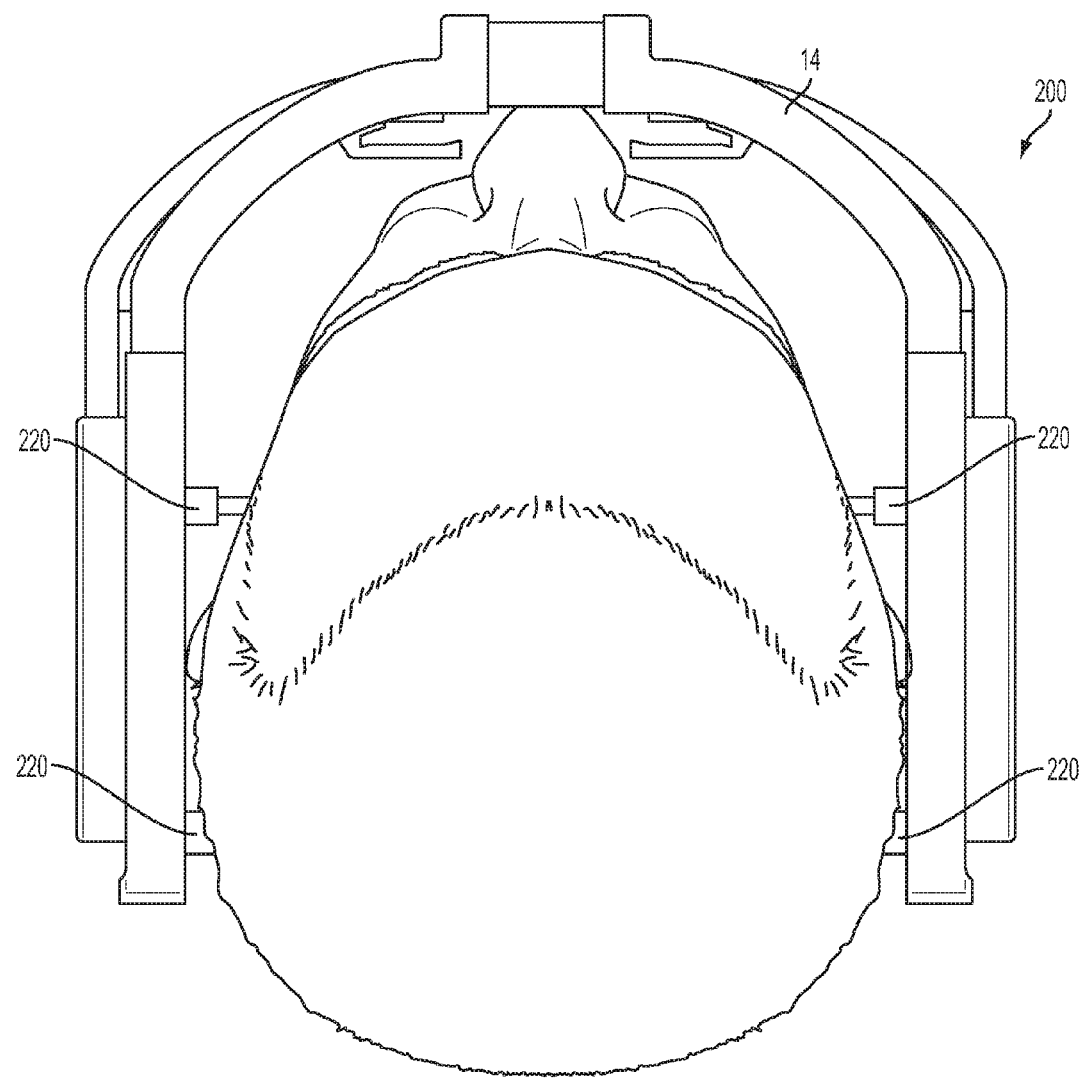
FIG. 14 depicts a top-down view of an example external distraction apparatus on the head of a patient.

FIG. 14 depicts a top down view of the external distraction apparatus 200 shown in FIG. 12. As shown, the apparatus 200 is fixed to the superior, lateral portions of the patient's 12 skull by means of a number of fixation pins 220. Also as shown, the apparatus 200 is shaped such that it surrounds and protects the patient's 12 head. The apparatus 200 is further configured in a compact manner. The curvature of the halo portion 14 of the apparatus 200 is such that the halo portion 14 does not extend excessively from the patient's 12 head. Additionally, the lateral sections of the halo portion 14 do not project excessively from the patient's 12 head. This helps to minimize the potential for snagging of the apparatus 200 as a patient 12 goes about their day. This makes the device less awkward for a patient 12 to wear. Preferably, however, there should be some space between the halo portion 14 and the head of the patient 12. In some embodiments, there may be approximately 25 mm-35 mm between the patient's head 12 and the halo portion 14. Such a gap may be important to accommodate for swelling.

Figure 15:
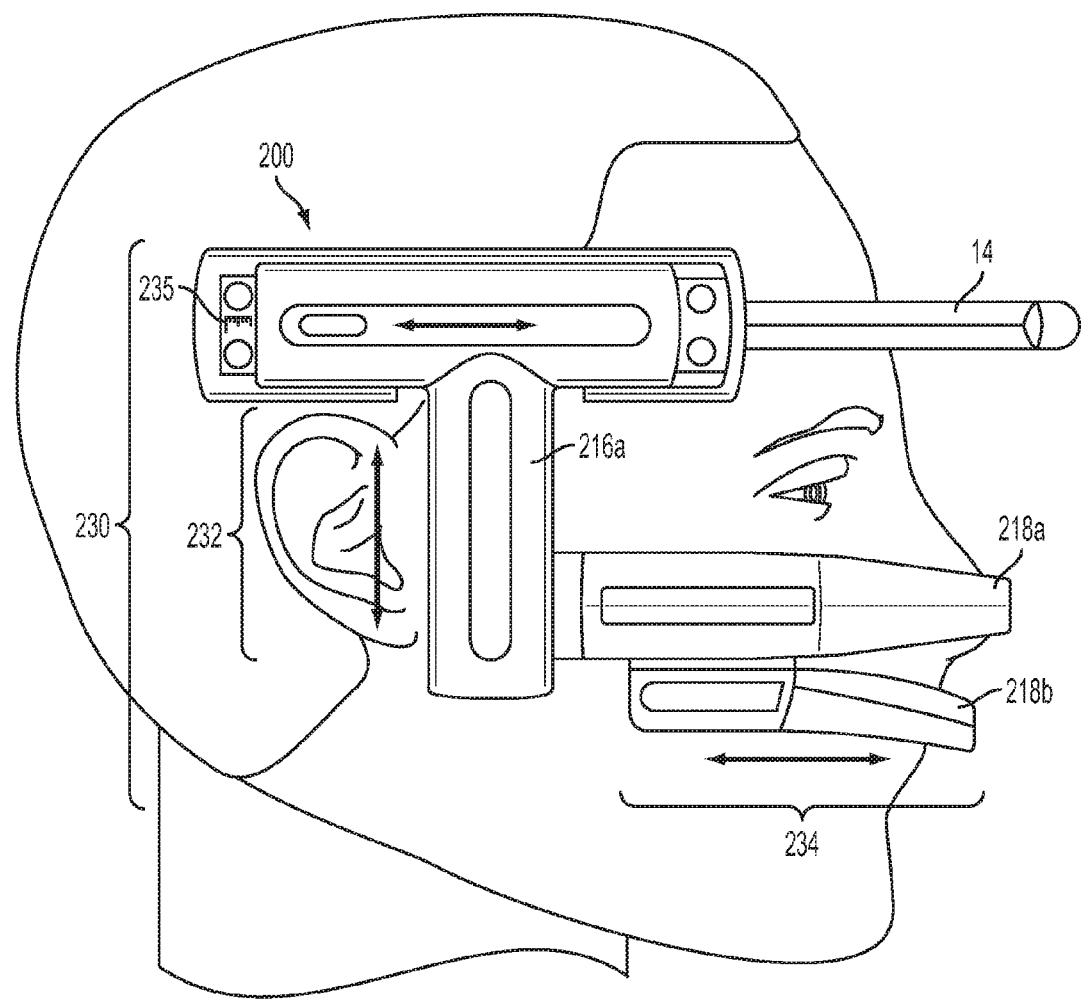
FIG. 15 depicts a side view of an example external distraction apparatus on the head of a patient.

FIG. 15 depicts a side view of the example external distraction apparatus 200 shown in FIG. 12. As shown, the side of the apparatus 200 may be divided into number of movable units 230, 232, and 234. Only one side of the apparatus 200 is shown for sake of brevity, however, the opposite side of the apparatus 200 (not shown), likewise, may be divided into a number of moveable units. In the example embodiment, the apparatus 200 is symmetrical and the opposite side of the apparatus 200 is divided into corresponding, counterpart moveable units which mirror those of the shown side. Each of the movable units 230, 232, and 234 may be selectively displaced in order to generate distraction along a desired distraction vector. The moveable units 230, 232, and 234 may move in conjunction with or in relation to their counterpart moveable units on the opposite side of the apparatus 200. Additionally, one or more of the moveable units 230, 232, and 234 may form a sub-unit of a larger movable unit.

In the exemplary embodiment shown, the first moveable unit 30 includes the entire upright body 216a and arm members 218a, b. The second moveable unit 232 and third moveable unit 234 are sub-units of the first moveable unit 230. The entirety of the first moveable unit 230 may be selectively displaced in relation to the stationary halo portion 14 of the apparatus 200 along a first displacement direction or axis. With respect to the page, the first displacement axis is roughly horizontal. Since the second moveable unit 232 and third moveable unit 234 are sub-units of the first moveable unit 230, displacement of the first moveable unit 230 also causes displacement of the second moveable unit 232 and third moveable unit 234 along the first displacement axis.

The second moveable unit 232 includes an inferior portion of the upright body 216a and the entire arm member 218a, b. Additionally, the third moveable unit 234 is a sub-unit of the second moveable unit 232. The entirety of the second moveable unit 232 may be displaced in relation to the halo portion 14 of the apparatus 200 and the remaining portion of the first moveable unit 230. The second moveable unit 232 may be displaced along a second displacement direction or axis. The second displacement axis may be substantially perpendicular to the first displacement axis. With respect to the page, the second displacement axis is roughly vertical. Since the third moveable unit 234 is a sub-unit of the second moveable unit 232, displacement of the second moveable unit 232 also causes displacement of the third moveable unit 234 along the second displacement axis.

The third moveable unit 234 includes the arm member 218b. The entirety of the third moveable unit 234 may be displaced in relation to the halo portion 14 of the apparatus 200 and the remaining portions of the first and second moveable unit 230, 232. The third moveable unit 234 may be displaced along a third displacement direction or axis. The third displacement axis, in the example embodiment, is offset and parallel to the first displacement axis. As shown, the third moveable unit 234 may be displaced to control rotation of the distracted portion of the craniofacial skeleton.

The moveable units 230, 232, and 234 may be displaced using any suitable means. In some embodiments, the moveable units 230, 232, and 234 may be displaced by a user via manual actuation. In such embodiments, a user may interface with a jack screw, rack and pinion, or other displacement mechanism to effect displacement of a desired moveable unit. Such an arrangement may be similar to those described above in relation to FIGS. 4-7. In some embodiments, one of more of the moveable units 230, 232, and 234 may be displaced in an automated manner. For example, some embodiments may include one or more motors and control electronics to displace a desired moveable unit. In some embodiments, all of the moveable units 230, 232, and 234 may be displaced in an automated manner. In embodiments where one or more of the moveable units 230, 232, and 234 is displaced in an automated manner, there may be a manual override for each such moveable unit 230, 232, and 234. Other displacement means may also be used.

Also, as shown in the example embodiment in FIG. 15, the apparatus 200 may include a number of visual distraction references 235. These visual distraction references 235 may allow a user to visually monitor the amount of displacement that has occurred for each of the moveable units 230, 232, and 234 of the apparatus 200 and check to ensure that movement is, in fact, occurring. In the example embodiments, the visual distraction references 235 are spaced reference markings or lines similar to those found on a ruler. In other embodiments, the visual distraction references 235 may differ.

Figure 16:
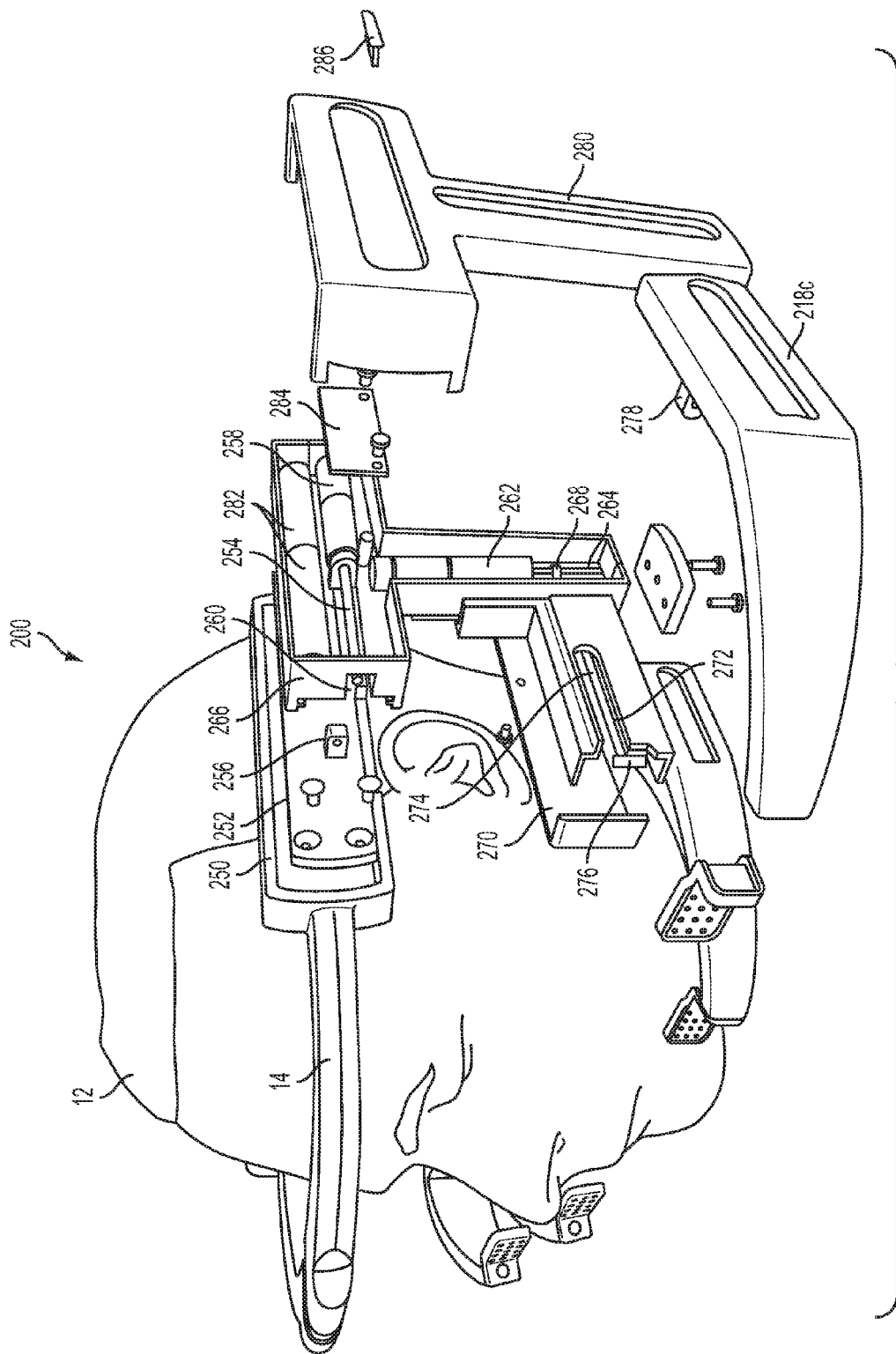
FIG. 16 depicts an exploded view illustrating example actuation components for moveable units of an external distraction apparatus.
Figure 17:
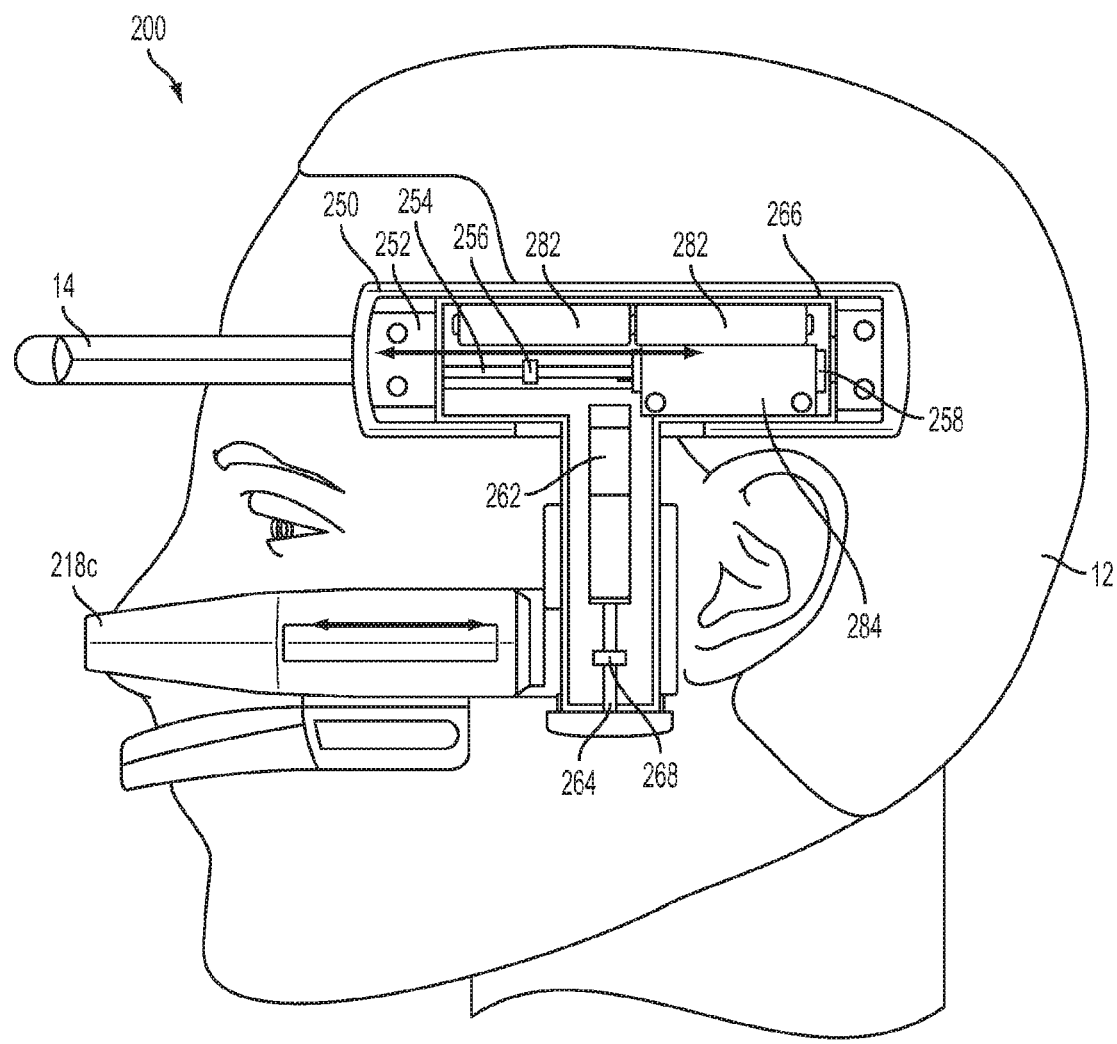
FIG. 17 depicts a partially-assembled, side view of the external distraction apparatus shown in FIG. 16.

FIG. 16 depicts an exploded view of example actuation components for the moveable units 230, 232, and 234 (see, for example, FIG. 15) of the apparatus 200. Referring also to FIG. 17 a partially assembled, side view of the apparatus 200 including the actuation components is shown. As shown, the example actuation components are configured to allow for powered and/or automated actuation. In alternate embodiments, manual actuation components (e.g. jackscrews and nuts, rack and pinions, etc.) may be used. As shown, a stationary block 250 is included in the lateral section of the halo portion 14 of the external distraction apparatus 200. A receiving plate 252 may be fixedly attached to the stationary block 250. As shown, the receiving plate 252 includes a first nut 256. The first nut 256 may operatively engage with a first lead screw 254 driven by a first motor 258.

As shown, the first motor 258 and first lead screw 254 may reside in a superior housing 266. In the example embodiment, the superior housing 266 may slidingly engage with, and be placed over the receiving plate 252. The sliding interface between the superior housing 266 and the receiving plate 252 may be any suitable sliding interface. As shown in FIG. 16, the sliding interface may be a rail interface such as a dovetail interface, tongue in groove interface, or the like. In other embodiments, rollers, ball bearings, a geared interface which allows for linear motion such as a rack and pinion type arrangement may be employed. As the first motor 258 produces rotation in the first lead screw 252, the first lead screw's 252 engagement with the nut 256 will cause the superior housing 266 to displace relative to the receiving plate 252. As shown, this displacement may be effected along the first displacement axis described above in relation to FIG. 15.

The superior housing 266 may also enclose a second motor 262 and an associated second lead screw 264. The second lead screw 264 may interface with a second nut 268. The second nut 268 may be attached to an inferior housing 270. As shown, the inferior housing 270 may slidingly engage the superior housing 266. The sliding interface between the inferior housing 270 and superior housing 266 may be any suitable variety of sliding interface. Any other suitable interface, such as any of those described supra may also be used. In some embodiments, the sliding interface may be a rail interface. Additionally, as shown, a slot is removed from the superior housing 266 to allow for the second nut 268 to extend into the superior housing 266 and travel along the length of the second lead screw 264. As the second motor 262 rotates the second lead screw 264, the second nut 268 will advance or retreat down the length of the second lead screw 264. This will cause the attached inferior housing 270 to displace as well. As shown, this displacement may be relative to the position of the superior housing 266 and may be effected along the second displacement axis described above in relation to FIG. 15.

The inferior housing 270 may enclose a third motor 272. The third motor 272 may be associated with a third lead screw 274. Due to spatial constraints, the third lead screw 274 (or any other lead screw if advantageous) may receive its rotational input via an intermediary gearing assembly 276 or other rotation to rotation or gearing arrangement. The third lead screw 274 may interface with a third nut 278. As shown, the third nut 278 is located on the inside face of the arm member 218c. The arm member 218c may slidingly engage with the inferior housing 270. Any suitable sliding interface may be used. In some embodiments, the sliding engagement may be a variety of railed engagement as depicted in FIG. 16. Also as shown, there may be a slot in the inferior housing 270 through which the third nut 278 may extend into the inferior housing 270 and interact with the third lead screw 274. Rotation of the third lead screw 274 may cause the third nut 278 to advance or retreat about the length of the third lead screw 274. This movement of the third nut 278 will also cause movement of the arm member 218c. The displacement of the arm member 218c may be relative to the inferior housing 270 and may be effected along the third displacement axis described above in relation to FIG. 16.

To power the first, second and third motors 254, 262, and 272 one or more power source may be included. In some embodiments, the power source may be one or a number of batteries 282. The one or more batteries 282 may be included within the external distraction apparatus 200 in some embodiments. In the example embodiment, two batteries 282 are shown housed within the superior housing 266. In embodiments where the batteries 282 are included within the external distraction apparatus 200, it may be desirable that the batteries 282 are sufficient to power the apparatus 200 for the entire distraction procedure. Alternatively, it may be desirable that the batteries 282 are rechargeable batteries which may be recharged without disassembly of the apparatus 200.

Figure 18:
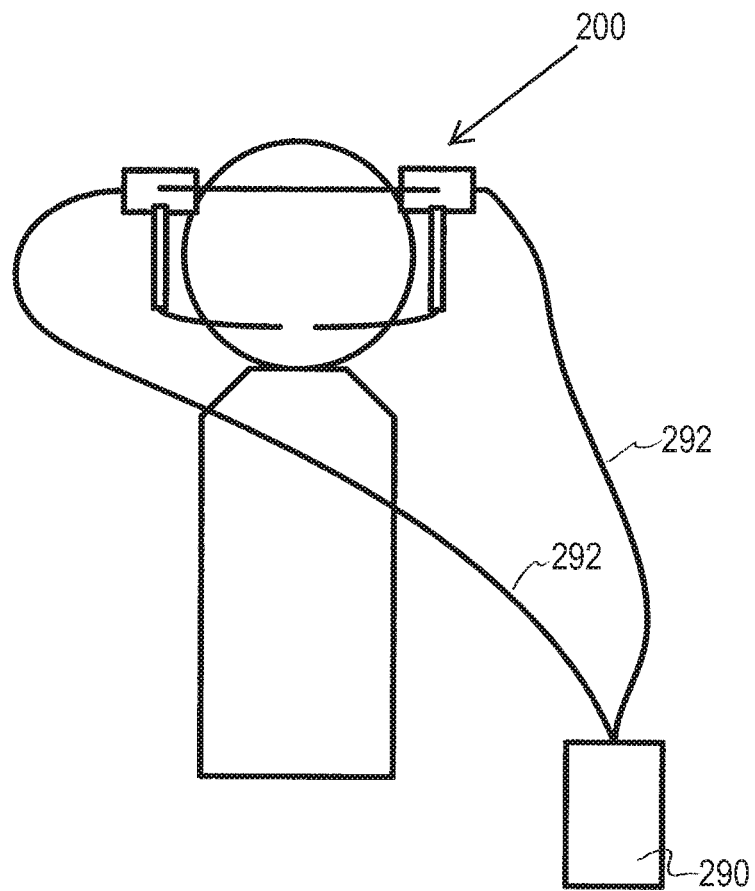
FIG. 18 depicts a representation illustration of an external distraction apparatus which is connected to a separate housing.

Referring now also to FIG. 18, in other embodiments, the power source may be located in a separate housing 290 which provides power to the apparatus 200 via a wired connection 292. Such an arrangement may allow the weight of the batteries 282 to be removed from the apparatus 200. Additionally, such an arrangement may allow the apparatus 200 to be less bulky as the apparatus 200 does not need to include space for a battery or batteries 282 to be housed in. In embodiments where power may be provided to the apparatus 200 via a wired connection 292 from a separate housing 290, the wired connection 292 to one or both the apparatus 200 or separate housing 290 may include a breakaway (not shown). Such a breakaway may be configured to allow the connection to be gracefully broken in the event of a snag. This may be desirable to minimize the risk of a snag introducing drift or pulling the apparatus 200 out of the desired alignment or orientation.

To control operation of the first, second and third motors 254, 262, 272, control circuitry may be included. The control circuitry may be included within the external distraction apparatus 200 in some embodiments. In embodiments with a separate housing 290, the control circuitry may also be disposed within the separate housing 290. In the example embodiment in FIG. 16 a PCB 284 is included in the apparatus 200. The PCB 284 may include the various control circuitry (e.g. processor, programmable logic device, memory, safety circuitry, etc.) for the external distraction apparatus 200.

In some embodiments, a distraction regimen may be stored on a memory element, for example, on the PCB 284. Such a distraction regimen may include a distraction schedule and distraction distances to be achieved at each increment in a distraction schedule. The distraction regimen may include a separate distraction schedule and distraction distances for each motor included in the apparatus 200. Such a distraction regimen may be used to execute automated micro-distraction during a craniofacial distraction procedure. The distraction regimen may be loaded onto a memory element via a serial bus (e.g. USB). A USB port cover 286 for a USB bus is shown in the example embodiment in FIG. 16.

In various embodiments, the superior housing 266 and/or inferior housing 270 may include one or more additional components. For instance, some embodiments may include a bearing support (not shown in FIG. 16) for one or more of the first, second or third lead screw 254, 264, 274. In some embodiments, one or more sensors (not shown in FIG. 16) may be included in the superior housing 226 and/or inferior housing 270. The sensors may be used for one or more of the following: to monitor the displacement of the superior housing 266, monitor displacement of the inferior housing 270, monitor rotation of the motor 258, 262, 272 shafts, monitor rotation of the lead screws 254, 264, 274, etc. The sensors may, for example, be any suitable variety of encoder such as, but not limited to, one or more of the following: linear encoder, rotary encoder, etc. In some specific embodiments, a magnetic rotary encoder may be associated with each motor 258, 262, 272 and a second magnetic rotary encoder may be associated with each lead screw 254, 264, 274 to provide a redundancy check. Additionally, in some embodiments, one or more manual override point(s) 260 may be included. In the example embodiment shown in FIG. 16 a manual override point 260 is included in the side of the superior housing 266 to allow a user to access and manually rotate the first lead screw 254 in the event of a first motor 258 failure. Additional manual override points 260 may be included for each actuator in the external distraction apparatus 200.

When fully assembled, a housing cover 280 may be attached to the external distraction apparatus 200. The housing cover 280 may enclose the superior housing 266 and any components (e.g. motors 258, 262, lead screws 254, 264, batteries 282, etc.) associated with the superior housing 266. Also when fully assembled, the arm member 218c may act as a cover for the inferior housing 270. In the partially assembled view shown in FIG. 17, the housing cover 280 is not shown, however, the arm member 218c is shown in its assembled location on the external distraction apparatus 200.

Figure 19:
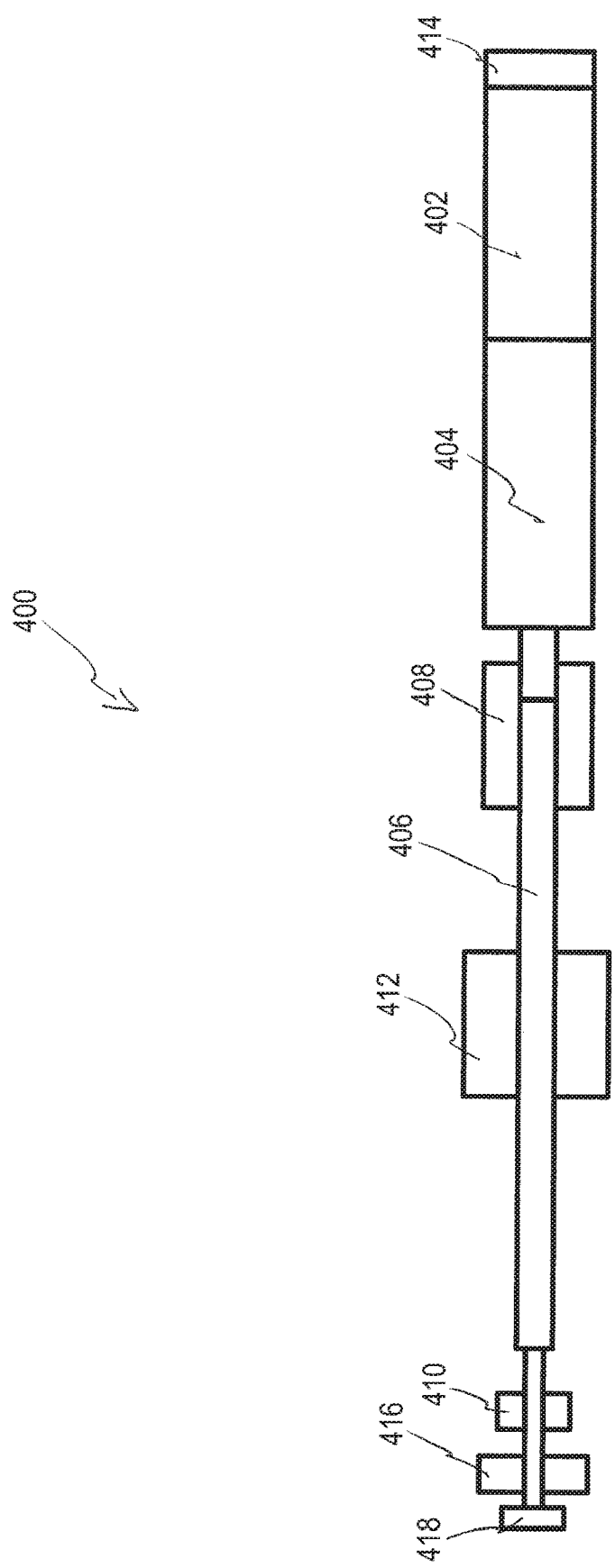
FIG. 19 depicts a block diagram or an actuator arrangement which may be used in an external distraction apparatus.

FIG. 19 depicts an example block diagram for an actuator arrangement 400. The actuator arrangement 400 may, for example, be used in the example external distraction apparatus 200 depicted and described above. As shown, the actuator arrangement 400 includes a motor 402. The motor 402 may be any suitable variety of motor, for example, a brushed DC motor in some specific embodiments. The motor 402 may be connected to a gear reduction assembly 404. In some embodiments, the gear reduction assembly 404 may include a planetary gearbox. The gear reduction assembly 404 may, in some specific embodiments, have a reduction ratio of 1000:1. In other embodiments, the gear reduction assembly 404 may not be included or the reduction ratio may differ. The output of the gear reduction assembly 404 may be coupled to a lead screw 406 by means of a coupling 408. The lead screw 406 may also be supported by a bearing 410. As the lead screw 406 rotates, a nut 412 on the lead screw 406 may be caused to travel along the length of the lead screw 406. Alternatively, the nut 412 may be fixed, and the housing in which the motor 402, lead screw 406, etc. is mounted may be causes to move via lead screw 406 rotation.

As shown, the actuator arrangement 400 includes a first sensor 414. The first sensor 141 may be a first encoder disposed and configured to track motor 402 revolutions. The actuator arrangement 400 also includes a second sensor 416. The second sensor 416 may be a second or safety encoder. The second sensor 416 may be disposed and configured to track lead screw 406 revolutions. Thus, in some embodiments, the sensors 414, 416 are redundant sensors and may be used in a redundancy check to ensure proper function. In the event that the sensors 414, 416 report values that do not reconcile with one another, an error state or fail-safe mode may be entered and power may be cut to the motor 402. In some embodiments, the sensors 414, 416 may need to fall outside of a predetermined range or proportionality of one another before an error state is entered.

In some specific embodiments, the first sensor 414 may be a magnetic rotary encoder which generates a first number of pulses per revolution. The second sensor 416 may be a magnetic rotary encoder which generates a second, larger number of pulses per revolution. This may be desirable in configurations with a gear reduction assembly 404 with a large reduction ratio. In embodiments where the actuator arrangement 400 is used in an external distraction apparatus 200 (see, for example, FIG. 12) this may avoid a scenario where a distraction takes place without generating a pulse from the second sensor 416.

In various embodiments, one or more additional sensors may be included. For example, some embodiments may include a force sensor. The force sensor may be any suitable variety of force sensor. Suitable force sensors may include, but are not limited to, a strain gauge affixed to a loaded, compliant member in the load path between the actuator and the distraction site. In embodiments where the actuator arrangement 400 is used in an external distraction apparatus, a force sensor may be used to ensure proper function of the apparatus. For example, if the force read by the sensor is above a predetermined threshold, an error state or fail-safe mode may be entered and power may be cut to the motor 402. This may be particularly desirable in embodiments where there is a large amount of gear reduction. Additionally, having a log of force values from an actuator arrangement 400 of an external distraction apparatus may be useful for investigational study and other purposes. In some embodiments, a force sensor may be associated with an end of the lead screw 406. In some embodiments, a force sensor such as a force sensitive resistor may be disposed between the motor 402 and gear reduction assembly 404. In such embodiments, the gear reduction assembly 404 may engage with the motor 402 in such a way that force may be exerted through the gear reduction assembly 404 to the force sensitive resistor.

In a specific exemplary embodiment, one or more of the sensors 414, 416 may be force sensors that are fed into a processor (e.g., processor 532 or programmable logic device 534) to facilitate utilization of a predetermined force profile. One or more of the sensors 414, 416 may be both a rotary encoder and a force sensor.

In the event of a failure, the actuator arrangement 400 includes an override point 418 which may be used to manually rotate the lead screw 406. The override point 418 may be any suitable variety of override point. In some embodiments, the override point 418 may be an appropriately shaped head which may be engaged with a screwdriver, wrench or the like. Such an override point 418 would allow a user to manually rotate the lead screw 406 and effect distraction if the actuator arrangement were to be incorporated into an external distraction apparatus 200 (see, for example, FIG. 12).

Figure 20:
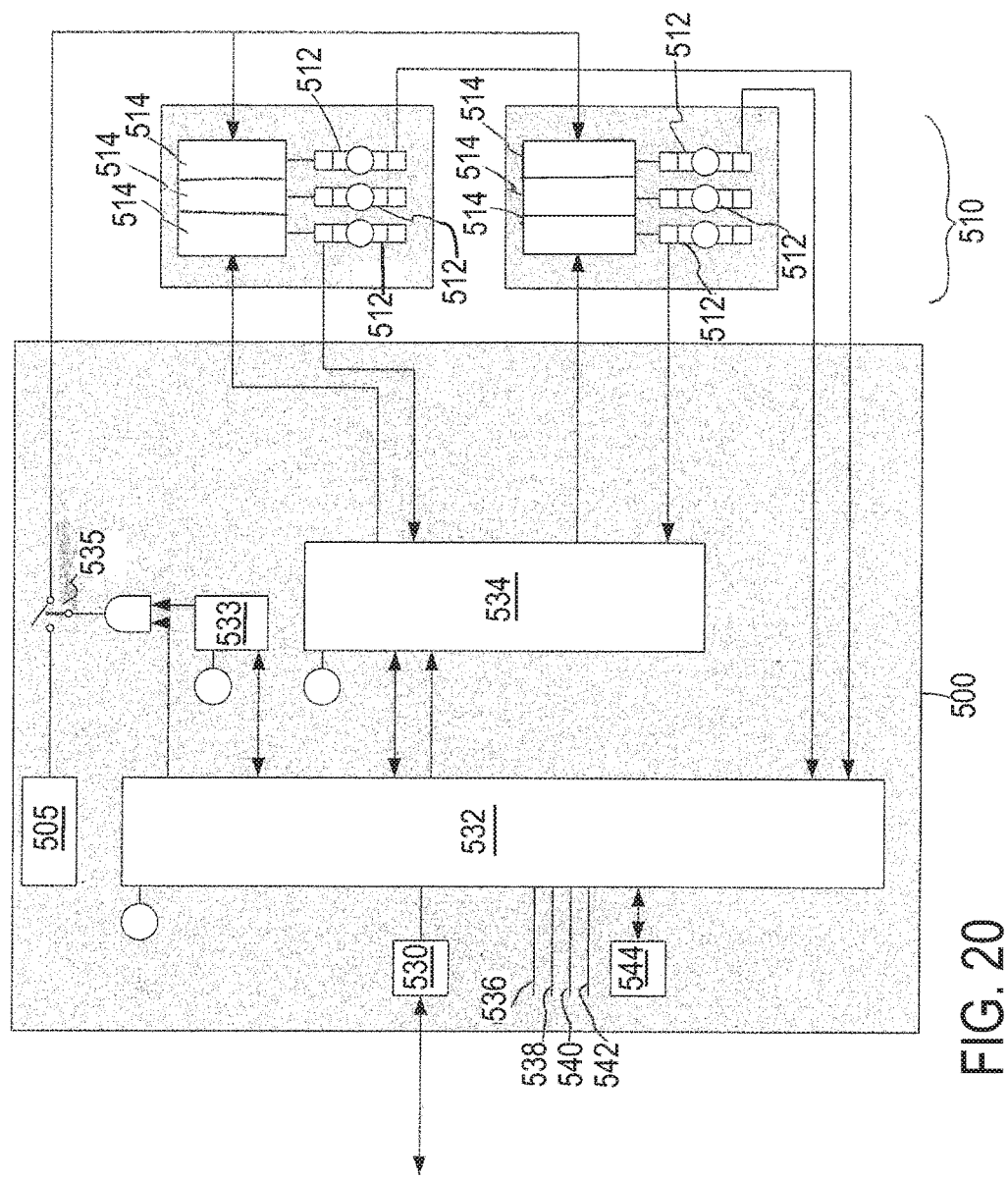
FIG. 20 depicts a schematic diagram illustrating an example electrical architecture for an external distraction apparatus.

An example block diagram of the electrical architecture for a controller 500 and external distraction apparatus 510 is shown in FIG. 20. The example apparatus 510 has three motors 512 on each side of the head, for a total of six motors 512. The motors 512, in the example embodiment, have integrated magnetic encoders whose outputs are fed-back to the controller 500. The motors 512 may be driven by H-bridges 514 as shown. The H-bridges 514 may be populated on two small PCBs, one for each side of the head. The controller 500 may precisely turn motor 512 shafts in a desired direction using the H-bridge control inputs and encoder feedback. Turning of the motor 512 shafts may cause relative movement of one part of the apparatus 510 to another part of the apparatus 510. This movement may be transmitted to the craniofacial skeleton through a bone mounting element attached to a portion of the craniofacial skeleton. Thus, by turning the motor 512 a bone movement or distraction may be performed. Additionally, a timer may be included so that the controller 500 may power the motors 512 at predetermined distraction intervals. By making the distraction interval sufficiently small, distractions may be performed in a continuous or near continuous manner.

At the beginning of the treatment, distraction parameters for each motor 512 may be written to the controller 500 through an interface 530 with, for example, a computer, tablet, smartphone, or the like. The interface 530 may be any suitable interface. In some specific embodiments, the interface 530 may be an RS232 interface or USB interface. The distraction parameters may be specified in a target number of encoder pulses per distraction. The distraction parameters may be stored in memory, for example, in an EEPROM (internal or external).

The controller 500 may be programmed to wake up at a predetermined distraction interval and turn each of the motors 512 according to the distraction parameters. As a motor 512 is turned, the controller 500 may count feedback pulses from the encoder. The controller 500 may stop powering the motor 512 when a target number of encoder pulses has been reached. When the motor 512 stops running, the encoder count from that distraction may be added to the previous counts from previous distractions. The sum may be recorded as a running total. The counts and running total may be stored in memory. This process may be repeated for each of the six motors 512. Once completed, the controller 500 may go back to sleep to conserve power. Power to the apparatus 510 may be disabled when the controller 500 is sleeping. Power for the controller 500 and apparatus 510 may be stored in one or more battery or batteries 505. Running totals may be read from the memory and through the interface 530 to monitor progress.

In the example embodiment in FIG. 20, the controller 500 includes a primary processor 532 and a programmable logic device 534. Both the primary processor 532 and programmable logic device 534 check each other and must agree before any distraction is made. If there is a fault, either device can disable the motors 512. The primary processor 532 performs bone distractions on a periodic basis according to distraction parameters stored in internal memory. The primary processor 532 uses the programmable logic device 534 as a slave device to perform the actual distraction.

As detailed above in relation to FIG. 19, each motor 512 may be associated with two encoders. One encoder may be integrated and coupled directly to the motor 512 shaft. This encoder is hereafter referred to as the primary encoder. The second encoder may be coupled to the motor 512 shaft (or lead screw) through a gear reduction. This encoder is hereafter referred to as the safety encoder.

While performing a distraction, the primary processor 532 checks the motor's 512 operation with safety encoder feedback pulses. The programmable logic device 534 interfaces with the primary encoder. Due to the gear reduction, one or more distractions might take place before ever getting a safety encoder pulse. The primary processor 532 multiplies the number of safety encoder pulses with the target distraction parameter, and compares this result with primary encoder pulse count. These two numbers should be within a predetermined range of or proportionality to each other, otherwise a fault condition may be detected and a fail-safe may be generated. In some embodiments, signals from the primary and safety encoders may be conditioned through a Schmitt trigger to provide a cleaner or less noisy signal.

The architecture may also include a Watchdog Timer 533 (hereafter, WDT). The WDT 533 may be powered by a supercapacitor (not depicted) to allow the WDT value to be maintained during a battery change. In some embodiments, including the embodiment shown in FIG. 20, a WDT 533 may be integral with the primary processor 532 and may be used to wake up the primary processor 532. Additionally or alternatively, a WDT 533 may be included external to the primary processor 532. In embodiments with two WDTs 533 one may wake up the primary processor 532 and the other may provide redundancy and may be used check to see that the amount of time slept was correct. If the primary processor 532 does not wake up on time, a fault condition may be detected and a fail-safe may be generated.

Internal memory may be included as well. In the example embodiment, the memory is integral with the primary processor 532, however, this need not be the case in all embodiments. This memory may be EEPROM (or any other suitable type of memory) and may store the distraction parameters for the apparatus 510. In some embodiments, each byte of data may be stored in redundant memory locations on the memory in the event of a data calculation or access fault. In a specific embodiment of the present disclosure, a list of possible example distraction parameters are shown in Table 1 as follows:

| Example Parameters | Description |
| --- | --- |
| Target distraction | Target number of primary encoder pulses per wake-up. |
| Target distraction multiplier | Number of times to repeat a six motor sequence of distractions |
| Primary encoder count | Running total of primary encoder pulses |
| Safety encoder count | Running total of safety encoder pulses |
| Elapsed time | Elapsed time since the beginning of the treatment |
| Sleep time | Time between waking up and performing a distraction. |

In the example embodiment, the primary processor 532 has four ADC inputs 536, 538, 540, 542. These ADC inputs 536, 538, 540, 542 may be used to check the supply voltages after powering up all the circuitry. A reference voltage supply 544 is also provided. In a specific embodiment, the ADC inputs 536, 538, 540, 542 may measure voltages from the battery or batteries 505, reference voltage supply 544, motor H-bridges 514, and programmable logic device 534.

The programmable logic device 534 may interface with the apparatus 510 and control power to various apparatus 510 components. The programmable logic device 534 may be used as a slave by the primary processor 532 to perform actual distractions. The programmable logic device 534 may enable power to the primary and safety encoders for each motor 512. The programmable logic device 534 may count primary encoder pulses. The programmable logic device 534 may also check for errors by monitoring the motor 512 activation sequence commands by the primary processor 532. There may be a degree of redundant control of distractions. For example, as shown, the primary processor 532 controls a motor voltage switch 535 which must be enabled for the motors 512 to be powered.

Figure 21:
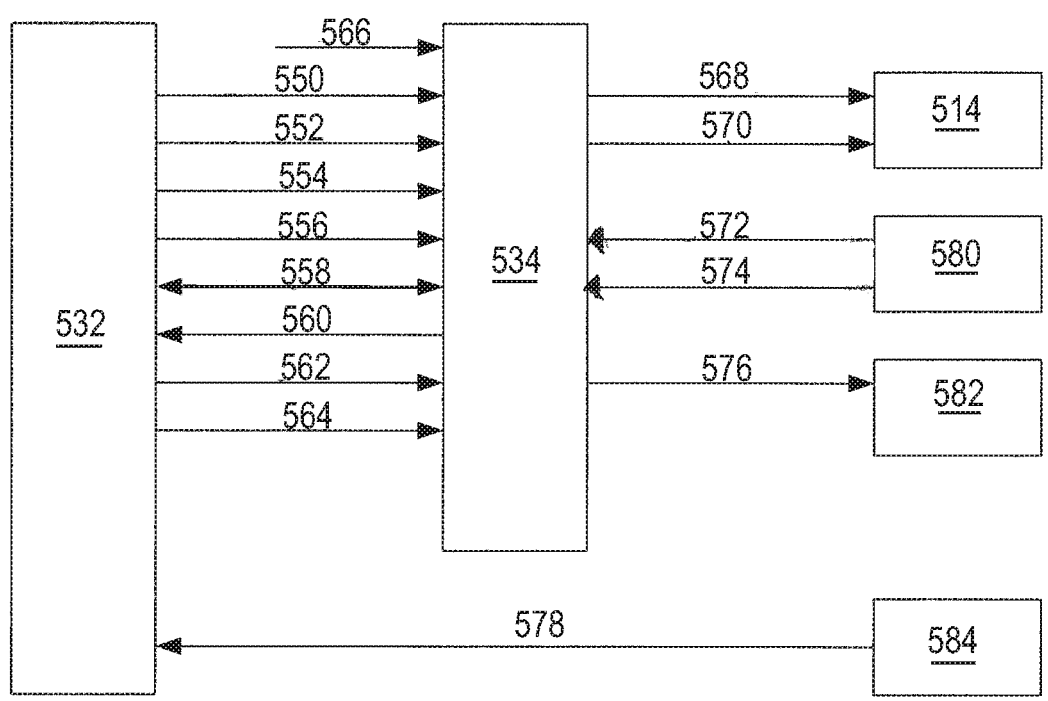
FIG. 21 depicts an electrical schematic diagram illustrating a primary processor, a programmable logic device, and components of an external distraction apparatus.

An example detailed block diagram detailing the interface between the primary processor 532, the programmable logic device 534, and components of an external distraction apparatus is shown in FIG. 21. As shown, a read/write enable line 550 runs from the primary processor 532 to the programmable logic device 534. A read high, write low line 552 also runs from the primary processor 532 to the programmable logic device 534. The primary processor 532 may use these lines 550, 552 to read from and write to the programmable logic device 534. Two register address lines 554, 556 are included as well. A bi-directional data line 558 is included between the primary processor 532 and the programmable logic device 534. A motor state line 560 is also included. This line runs from the programmable logic device 534 to the primary processor 532 and provides information about distraction progress. The motor state line 560 may, for example, be low when the motor is turning and go high when the distraction target has been reached. A clock line 562 extends from the primary processor 532 to the programmable logic device 534. The clock line 562 may transmit the clock signal from the primary processor 532 to the programmable logic device 534. A reset line 564 running from the primary processor 532 to the programmable logic device 534 is included. Additionally, a programmable logic device clock line 566 is included. The clock signal fed to the programmable logic device 534 through this line may be used in detection of all data edges and may be used to synchronize all logic carried out by the programmable logic device 534.

A positive enable line 568 is shown running from the programmable logic device 534 to the H bridges 514. The positive enable line 568 may be used to power the motors in a first direction. A negative enable line 570 is also included and runs from the programmable logic device 534 to the H bridges 514. This line 570 may be used to power the motors in the reverse direction. An A phase feedback line 572 and B phase feedback line 574 are also shown. These lines 572, 574 may convey an A phase and B phase output of the primary encoders 580 to the programmable logic device 534. An encoder power line 576 is included and conveys power to encoder power transistors 582 (e.g., MOSFETS). Additionally, a safety encoder feedback line 578 is included and transmits safety encoder 584 output to the primary processor 532.

Figure 22:
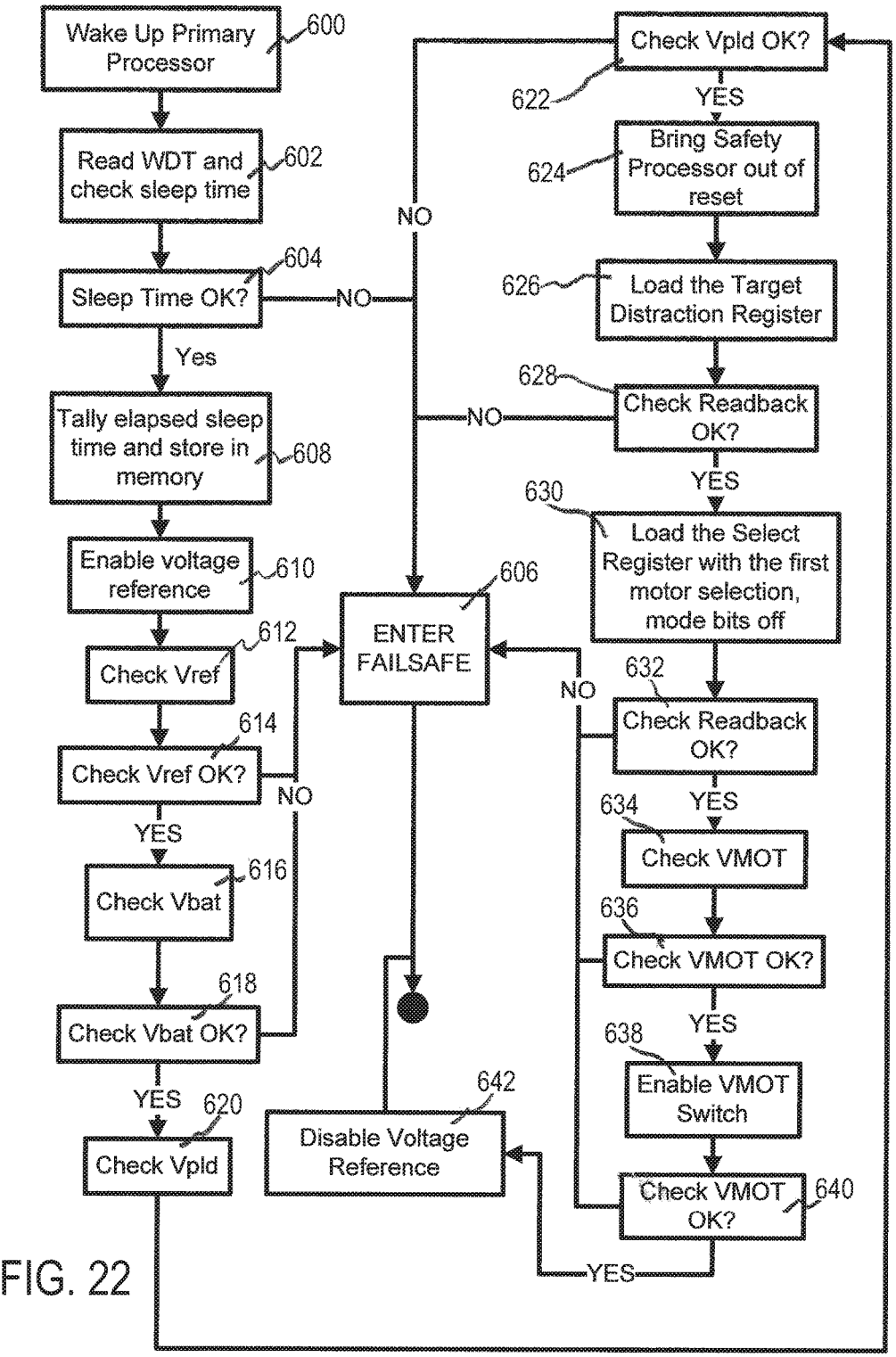
FIG. 22 depicts a flowchart detailing a number of example steps which may be used to wake up control components of an external distraction apparatus and ready the external apparatus for a distraction.

FIG. 22 depicts a flowchart detailing a number of example steps which may be used to wake up a primary processor and ready an external distraction apparatus for a distraction. In step 600 the primary processor may be woken up. This may occur after a predetermined sleep period has elapsed. The count from a timer clock may be used to track the duration of a sleep time for the primary processor. After the primary processor has been woken up, the sleep time may be checked by reading the count on a WDT in step 602. In step 604, the primary processor may determine that the sleep time is within a predetermined range of the programmed sleep period. If the sleep time is outside of the predetermined range, the device may proceed to step 606 and enter a failsafe mode. If the sleep time is within the predetermined range, the sleep time may be tallied and stored in memory in step 608.

A reference voltage source may then be enabled in step 610. Once enabled, in step 612 the primary processor may check the reference voltage "Vref" and ensure that it is within a predetermined range of the expected voltage in step 614. If the voltage is not within the predetermined range, the device may proceed to step 606 and enter a failsafe mode. If the voltage from the reference voltage source is within the range, the primary processor may check battery voltage "Vbat" in step 616 and ensure that it is within a predetermined range of the expected voltage in step 618. If the voltage is not within the predetermined range, the device may proceed to step 606 and enter a failsafe mode. The device may also issue a low battery alert. If the voltage from the battery is within the range, the primary processor may check programmable logic device voltage "Vpld" in step 620 and ensure that it is within a predetermined range of the expected voltage in step 622. If the voltage is not within the predetermined range, the device may proceed to step 606 and enter a failsafe mode. If the programmable logic device voltage is within the range, the primary processor may bring the programmable logic device out of reset in step 624.

The target distraction register may then be loaded on the programmable logic device in step 626. The primary processor may check readback from the loaded target distraction register in step 628. If the readback check fails, the device may proceed to step 606 and enter a failsafe mode. If the readback check is passed, a motor selection may be loaded onto the programmable logic device in step 630. All of the mode bits may be turned off in this step. That is, the motors and encoders may be off and the encoder counter may be set to zero. The primary processor may then check readback from the select register in step 632. If the readback check fails, the device may proceed to step 606 and enter a failsafe mode.

If the readback check is passed the primary processor may check motor voltage "VMOT" in step 634 and ensure that it is within a predetermined range of the expected voltage in step 636. Since the mode bits have been set to off, this should be a low voltage. If the voltage is not within the predetermined range, the device may proceed to step 606 and enter a failsafe mode. If the VMOT voltage is within an acceptable range, power to the motors may be enabled via a VMOT switch in step 638. The primary processor may, in step 640, then check the VMOT voltage again to ensure that it is within a predetermined range of an expected value. If the voltage is not within the predetermined range, the device may proceed to step 606 and enter a failsafe mode. If the voltage is within the predetermined range, the reference voltage source may be disabled in step 642.

Figure 23:
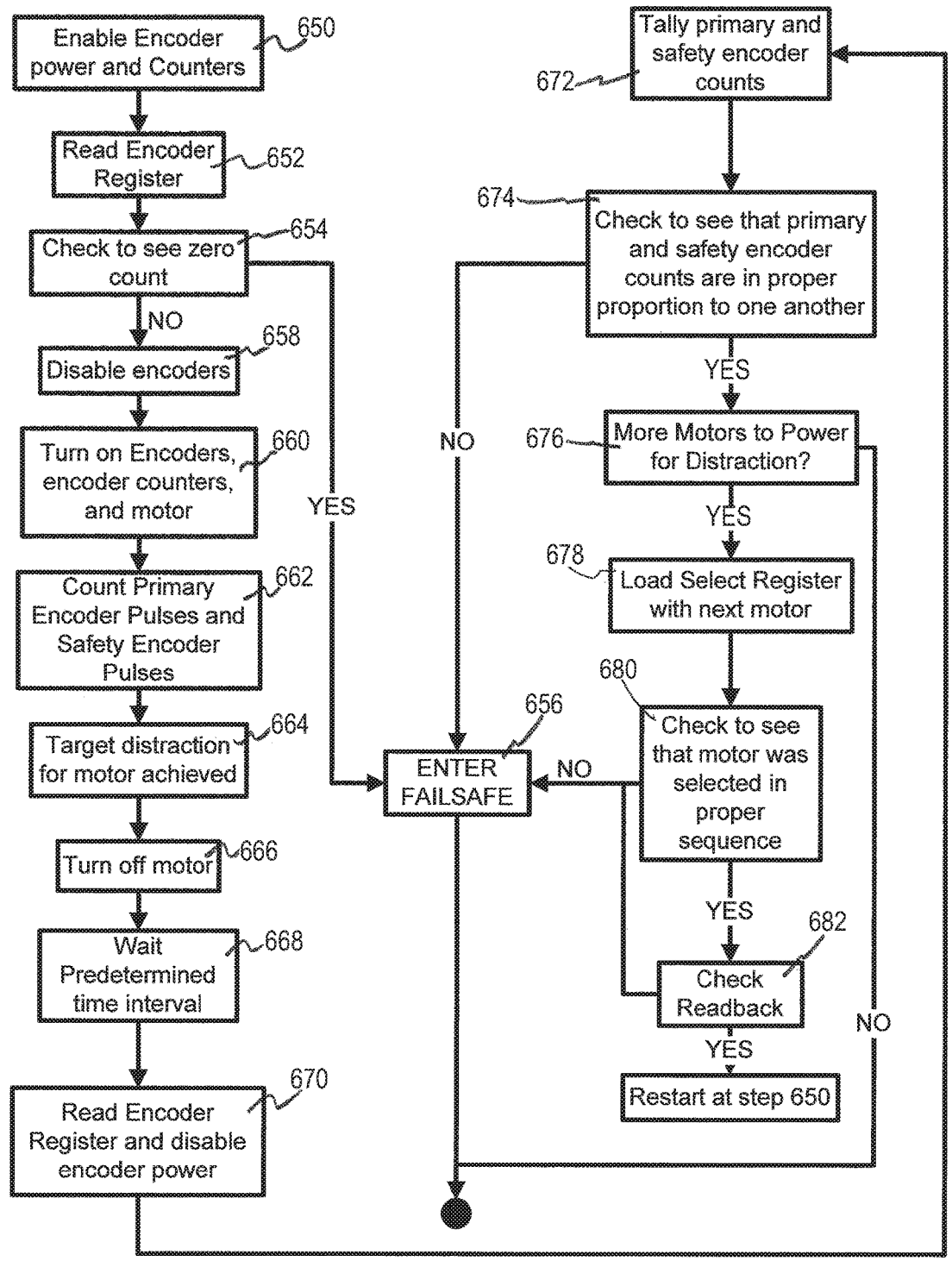
FIG. 23 depicts a flowchart detailing a number of example steps which may be used to perform a distraction with an external distraction apparatus in an automated fashion.

Once the device has been woken up and readied for distraction, the distraction may be performed by the device. FIG. 23 depicts a flowchart detailing a number of example steps which may be used to perform a distraction with an external distraction apparatus. In step 650, the power to the encoders may be enabled and the encoder counter may also be enabled. This may involve the primary processor setting the encoder mode bit to on in the select register of the programmable logic device. Setting the encoder mode bit to on, in turn, may cause the programmable logic device to power the encoders and start counting encoder pulses. Once the encoders are powered and the encoder counter has been enabled, the encoder register may be read in step 652 and checked to see that the encoder register has a count of zero (indicating no motor movement) in step 654. If the count does not read zero, the device may proceed to step 656 and enter a failsafe mode. If the encoder count reads zero, the encoders may be turned off in step 658. This may be accomplished by the primary processor changing the encoder mode bit to off in the select register of the programmable logic device.

The encoders, encoder counter, and power to the desired motor may be turned on in step 660. This may involve the primary processor setting the encoder and motor mode bits to on in the select register of the programmable logic device. This may cause the programmable logic device to enable encoder power and the encoder counter. It may also cause the programmable logic device to check a sign bit for the distraction (which indicates forward or reverse motor rotation). In response to the sign bit for the distraction, the programmable logic device may appropriately enable the proper H-bridge and power the motor. The programmable logic device may also signal to the primary processor that the motor is running. This may, for example, be accomplished by setting a motor state line 560 (see FIG. 21) low.

As the distraction takes place, primary encoder pulses may be counted by the programmable logic device and safety encoder pulses may be counted by the primary processor in step 662. The motor may be run until the target distraction has been achieved in step 664. Once the target distraction has been achieved, the motor H-bridge may be disabled in step 666 and the programmable logic device may signal to the primary processor that the target distraction value has been reached. This may, for example, be accomplished by setting a motor state line 560 (see FIG. 21) high. The device may then wait a predetermined time interval (e.g. 75ms) in step 668.

In step 670, the encoder registers for the primary and safety encoders may be read and stored in memory. The encoder mode bit may be then be set to off. The primary and safety encoder counts may be tallied and stored in memory in step 672. In step 674, the counts from the primary and safety encoders may be compared and checked to see that a proper relationship, for example, proportionality exists between them. If such proportionality is not present, the device may proceed to step 656 and enter a failsafe mode. If proper proportionality exists, the device may proceed to step 676 and check to see if there are more motors which need to be powered to make a distraction along the desired distraction vector.

If no further motors are to be powered, the distraction process may be finished. If additional motors are to be powered the device may proceed to step 678. In step 678, the select register of the programmable logic device may be loaded with a selection of the next motor to powered. In step 680, the programmable logic device may check to see that the motor loaded into the select register was selected in the appropriate sequence. If the motor was selected out of sequence the device may proceed to step 656 and enter a failsafe mode. If the correct motor was selected the primary processor may check readback from the select register in step 682. If the readback check fails, the device may proceed to step 656 and enter a failsafe mode. If the readback check is passed, the process may return to step 650 and proceed as described above.

Figure 24:
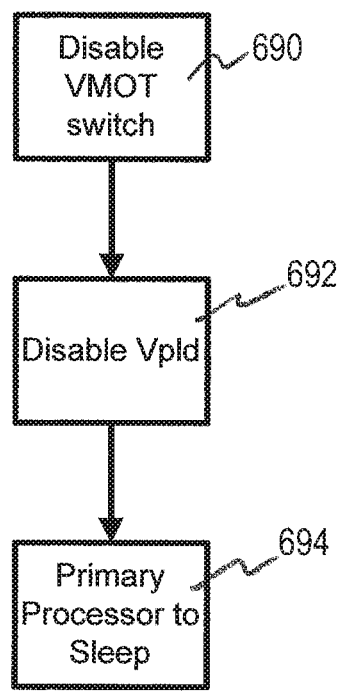
FIG. 24 depicts a flowchart detailing a number of example steps which may be used to put control components of an external distraction apparatus into a power saving state.

After a distraction has finished, the device may be put into a power save or conservation mode. FIG. 24 depicts a flowchart detailing a number of example steps which may be used to put an external distraction apparatus into a power save mode. In step 690, the primary processor may disable the VMOT switch. In step 692, Vpld may be disabled. In step 694, the primary processor may be put into a sleep state. In this state, only select components of the device may be powered. For example, clocks and timers for the device may be powered.

Figure 25:
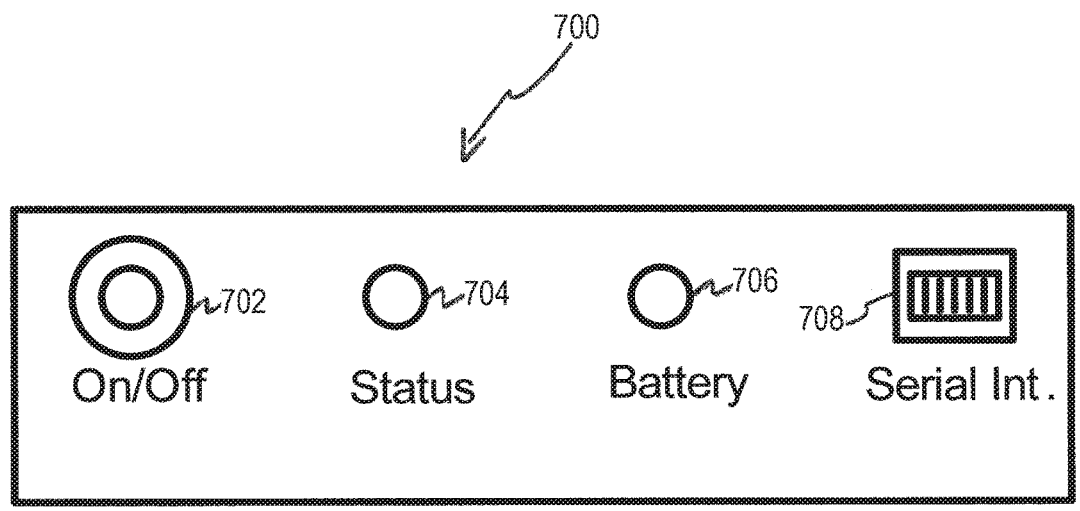
FIG. 25 depicts an example embodiment of a user interface for an external distraction apparatus.

FIG. 25 depicts an example embodiment of a user interface 700 which may be included on or associated with an external distraction apparatus, such as for example, the external distraction apparatus 200 shown and described in relation to FIGS. 12-18. In some embodiments, the user interface 700 may be disposed on a portion of the apparatus itself. In specific embodiments, the user interface 700 may be disposed on one of the two upright bodies 216*a, b* (see, for example, FIG. 8). In alternate embodiments, the user interface 700 may be on a separate housing. In specific embodiments, the user interface 700 may be disposed on the separate housing 290 described in relation to FIG. 18.

As shown, the user interface 700 may include a number of buttons, indicators, and/or interface ports. The example user interface 700 includes an on/off button 702. The example user interface 700 includes a status indicator 704 and a battery indicator 706. A serial interface port 708 is also included on the example user interface 700.

The on/off button 702 in the example embodiment is a hard button which may have to be physically depressed by a user. In other embodiments, the on/off button 702 may be a switch, toggle, or the like. The on/off button 702 may be used to power the device on and off. In some embodiments, the on/off button 702 may have to be held down for a predetermined period of time, pressed multiple times, or combination thereof in order to turn the device on or off. This may be desirable to avoid a bump or unintentional button press from turning the device on or off. In some embodiments, the on/off button 702 may be disabled after a distraction procedure has been initiated.

The status indicator 704 may be an illuminated indicator (e.g. one or more LED). The status indicator may light in various colors and/or patterns to indicate various states of an external distraction apparatus to a user. In a specific embodiment, the status indicator 704 may sporadically or periodically blink green when the apparatus is in sleep state. The status indicator 704 may also light solid green when a motor of the external distraction apparatus is being powered or when a distraction is being readied or performed. The status indicator 704 may additionally light solid red or blink red to indicate a fail-safe mode has been entered. In some embodiments, other states may be indicated by the status indicator 704. For example, the status indicator 704 may light yellow when the apparatus is communicating with a computer via the serial interface 708.

The battery indicator 706 may provide indication of battery charge to a user. The battery indicator 706 may be an illuminated indicator (e.g. an LED). In some embodiments the battery indicator 706 may only light in the event that a low battery condition exists. In such embodiments, the battery indicator 706 may light solid red or blink red.

The serial interface port 708 may allow a user to connect the apparatus to a separate device and communicate with that device. The serial interface port 708 may for example be used to connect the apparatus to a PC through which distraction parameters or other programming may be loaded onto the device. The serial interface 708 may also be used to extract data from memory locations on the device. For example, a user may extract data related to distraction progress (e.g. encoder count tallies) using the serial interface 708. The serial interface port 708 may also be used to provide power to the apparatus or charge the batteries of the apparatus in embodiments where the apparatus includes chargeable batteries. Any suitable serial interface (e.g. USB) may be utilized.

In alternative embodiments, the apparatus may instead or additionally include a display (not shown). The display may be used to display various information about the device or therapy to a user. For example, such a display may be used convey status or battery information to a user. In some embodiments, a user may use the display to view distraction progress related information. Accompanying such a display may be a number of buttons for navigation of various display screens.

In some embodiments, one or more speaker (not shown) may be included in the user interface 700. The speaker(s) may provide feedback to a user after button presses. The speaker(s) may provide audible indications to accompany or signal various statuses. The speaker(s) may also be used to provide audible indication of a low battery.

Figure 26:
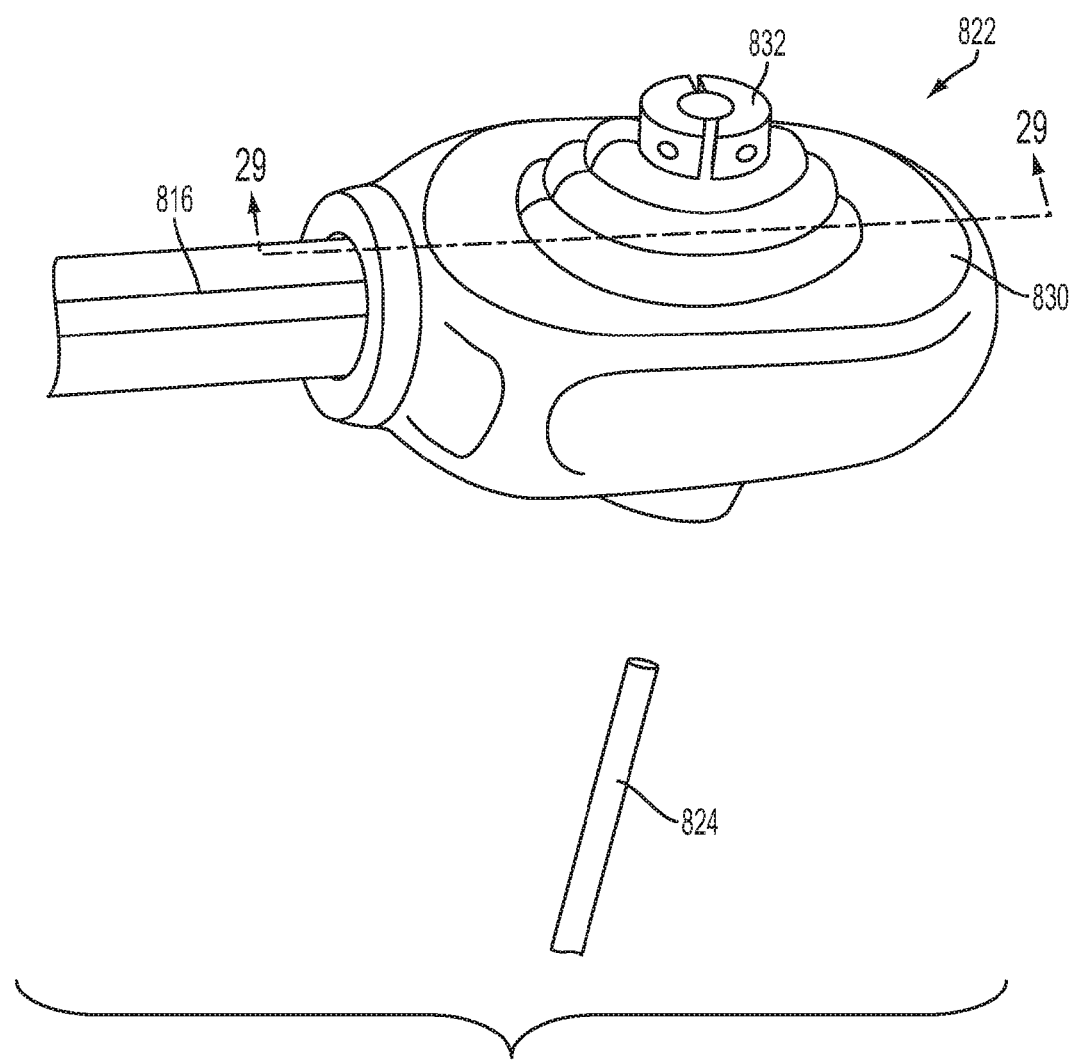
FIG. 26 depicts an example coupling element which may be included in an external distraction apparatus.

FIG. 26 depicts an example embodiment of a coupling element 822 which is adjustable. The coupling element 822 may be used as a coupling element in an external distraction apparatus such as any other those described herein. For example, the coupling element 822 may be a specific example of the coupling element 6 described in relation to FIG. 1 or may, for example, be used in place of the clamp coupling elements 22 in FIG. 2. As shown, the coupling element 822 may be placed on a rod 824. The rod 824 may, for example be any of the transcutaneous rods described and shown herein.

Figure 27:
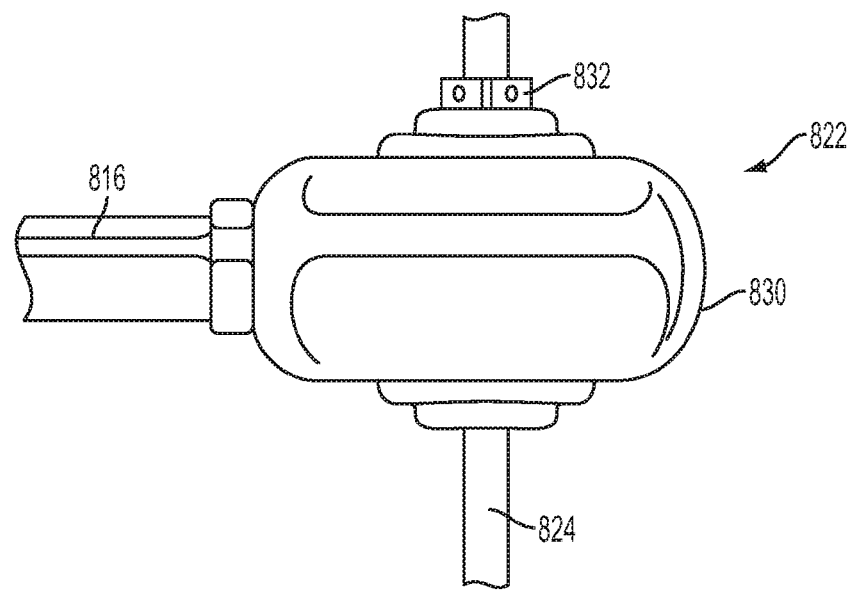
FIG. 27 depicts an example coupling element coupled to a rod.
Figure 28:
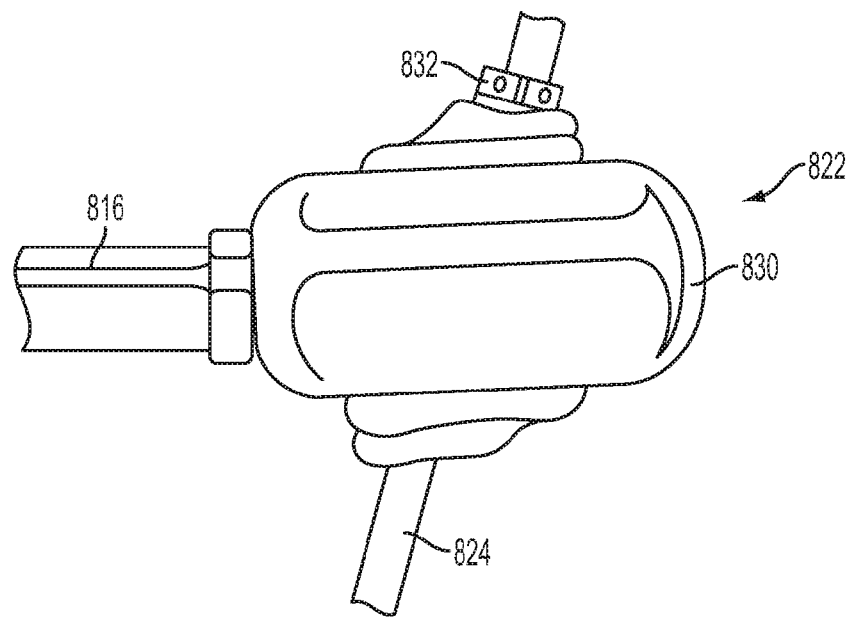
FIG. 28 depicts an example coupling element coupled to a rod.

The coupling element 822 may adjust such that it may fixedly and statically couple to a rod 824 which may be in a range of different spatial orientations. Referring now also to FIGS. 27 and 28 side views of a coupling element 822 coupled to rods 824 in different orientations are shown. After coupling to the rod 824, the coupling element 822 and rod 824 may be incapable of movement relative to one another.

As shown, the coupling element 822 includes a housing 830. The housing 830 is attached to an arm 816. The arm 816 may extend from a larger device or apparatus (e.g. an external distraction apparatus). The housing 830 and arm 816 in the example embodiment are stationary. A bearing 832 (best shown in FIG. 29) which is sized to slide over the rod 824 may extend through the housing 830. The bearing 832 may be displaced within the housing 830 in one or more degrees of freedom to accommodate a range of possible spatial orientations of the rod 824. The bearing 832 may then be fixed to the rod 824 and locked or frozen in place within the housing 830.

Figure 29:
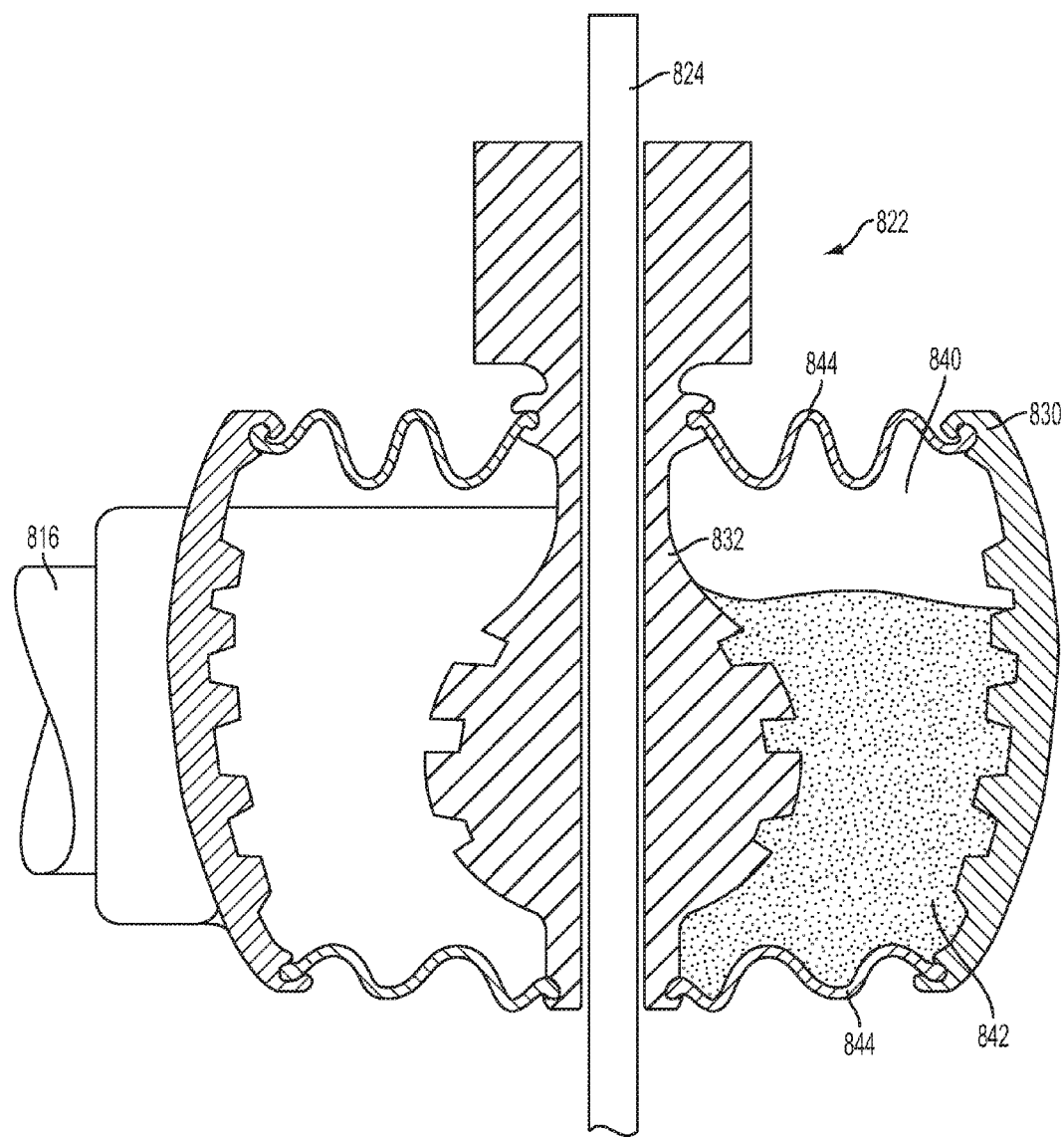
FIG. 29 depicts a cross-sectional illustration of the example coupling element shown in FIG. 26 taken at line 29-29 of FIG. 26.

FIG. 29 depicts a cross section view of an example coupling element 822 taken at line 29-29 of FIG. 26. As shown, the housing 830 for the coupling element 822 is hollow and includes an interior volume 840. The bearing 832 for the rod 824 may extend through the hollow portion of the housing 830. The remaining volume of the housing 830 or a portion of the remaining volume of the housing 830 may be filled with a fusible alloy 842. A membrane 844 may be included as part of the coupling element 822. The membrane 844 may serve to enclose and seal the interior volume 840. The membrane 844 may also attach to and hold the bearing 832 within the interior volume 840 of the housing 830.

The fusible alloy 842 may be any variety of such alloys known in the art. It may be preferable that the melting temperature of the alloy 842 be higher than ambient temperature ranges the coupling element 822 may experience. In embodiments where the coupling element 822 is to be used as part of an external distraction device, it may be desirable that the melting temperature of the fusible alloy 842 be sufficiently above body temperature. It may further be desirable that the fusible alloy 842 used is non-toxic. In some embodiments, the alloy 842 may be poured into the interior volume 840 in molten state during assembly. Alternatively, pellets, chunks, blocks, or the like of solid alloy 842 may be placed into the interior volume 840 during assembly. The alloy 842 may be heated with a heating apparatus such as the heating apparatus 900 shown and described in relation to FIGS. 30 & 31. Alternatively, the fusible alloy 842 may be melted by submersing the coupling element 822 in hot or boiling water depending on the alloy 842 used.

The fusible alloy 842 used may, for example, be an indium-bismuth alloy. In some specific embodiments, the fusible alloy 842 may be a 66.3% indium, 33.7% bismuth alloy. Such an alloy may be desirable because the alloyed elements are substantially non-toxic. With a melting point of ~72° C. (162° F.) the alloy 842 is unlikely to melt in ambient conditions. Such an alloy would also be capable of melting by submersion of the coupling element 822 into hot or boiling water. Additionally, the melting point of the alloy 842 is not so high as to severely limit choice of membrane 844 material.

The membrane 844 may be made of any flexible, stretchable, and/or elastomeric material. Any suitable elastic polymer or rubber may be used. Preferably, the membrane 844 material is not porous and relatively durable. Also, it is desirable that the membrane 844 be made from a material which is not compromised at the melting point of the chosen fusible alloy 842. The membrane 844 may be formed with extra material, be pleated, or have a bellows or accordion-like structure such that it is expandable. This may help allow for easier movement of the bearing 832 within the interior volume 840.

When the alloy 842 is heated, the alloy 842 will melt (molten alloy 842 shown on the right side of the rod 824). It may be desirable that the housing 830 be made of a material with a high thermal conductivity to facilitate heating. When the alloy 842 has been melted, the bearing 832 may be free to move within the interior volume 840 of the housing 830. While the alloy 842 is molten, the bearing 832 may be manipulated such that it aligns with the rod 824. The bearing 832 may then be slid over the rod 824. As shown, the rod 824 is oriented substantially vertically, but is off center in relation to the interior volume 840 of the housing 830. The bearing 832 has been adjusted accordingly and slid over the rod 824.

The alloy 842 may then be allowed to cool and solidify (solidified alloy 842 shown on the left side of the rod 824). When the alloy 842 cools, the bearing 832 is effectively frozen in place within the interior volume 840 of the housing 830. Depending on the alloy 842, the alloy 842 may expand as it solidifies as depicted in the example embodiment shown in FIG. 29. If such an alloy 842 is used it may be desirable that the interior volume 840 only be partially filled with the alloy 842 during assembly. Alternatively, it may be desirable that the membrane 844 be capable of stretching or be pleated, bellows-like, etc. to accommodate the expansion. Once the alloy 842 is frozen, the rod 824 may be fixed in place (e.g. via a clamp) to prevent relative movement of the rod 824 and coupling element 822 in the axial direction of the rod 824. The rod 824 and coupling element 822 may then be incapable of movement relative to one another. Thus, linear and moment forces may be exerted through the coupling element 822 directly to the rod 824.

Figures 30, 31:
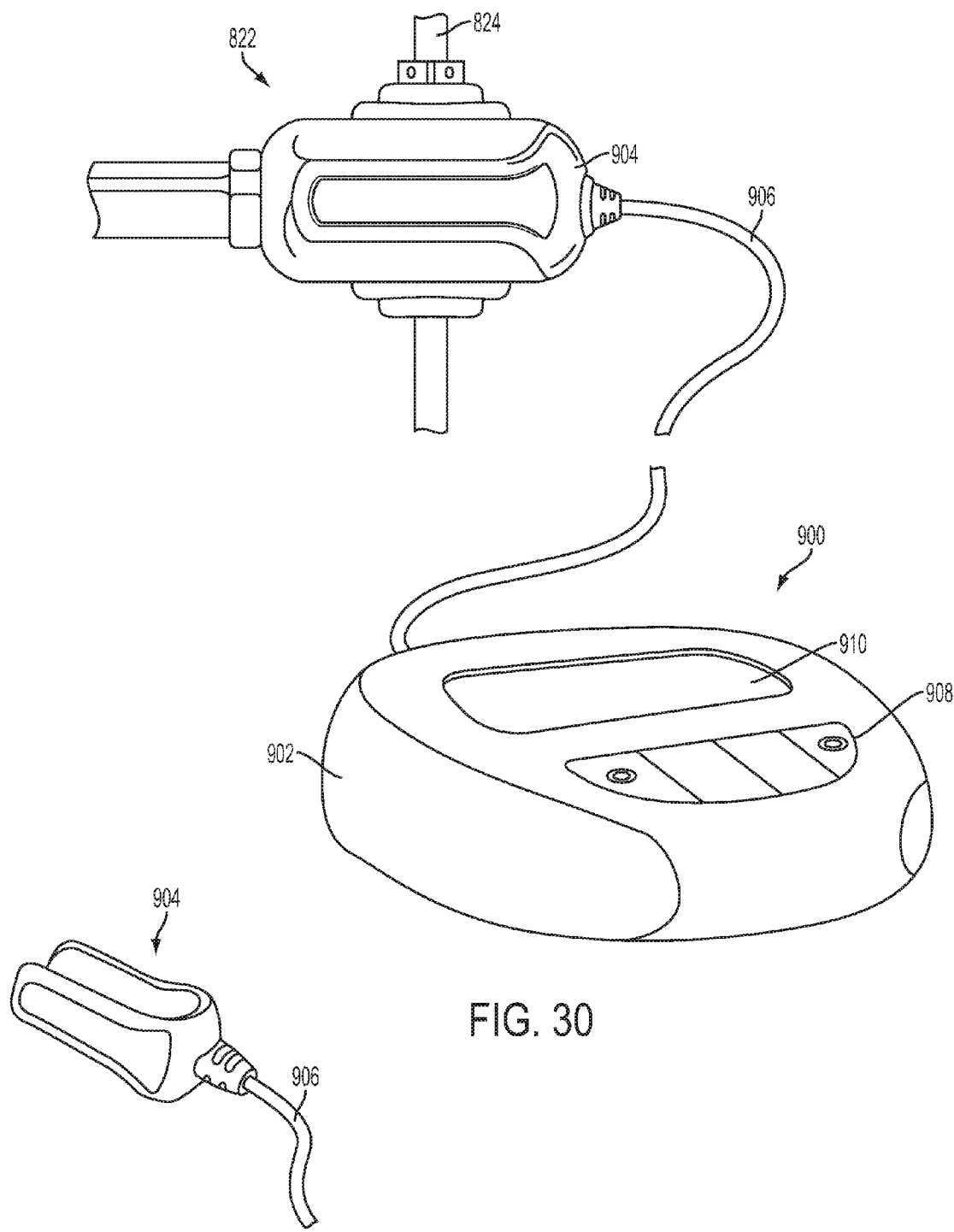
FIG. 30 depicts an example heating apparatus including a controller and a heating element.
FIG. 31 depicts a perspective view of an example heating element which may be included in a heating apparatus.

FIG. 30 depicts an example embodiment of a heating apparatus 900. The heating apparatus 900 may be used to heat a fusible alloy in a coupling element 822. As shown, the heating apparatus 900 includes a controller 902 and a heater or heating element 904. Referring also to FIG. 31, a top perspective view of the heater element 904 is shown. The controller 902 may be used to turn the heating element 904 on/off. Additionally, the controller 902 may be used to maintain the heating element 904 or a heated object at or near a specific temperature or within a desired temperature range. In the example embodiment, the heating element 904 and controller 902 are connected via a wired connection 906.

The heating element 904 may be any suitable variety of heating element. In some embodiments, the heating element 904 may be or include at least one of an induction heating element, resistive heating element, etc. In embodiments where the heating element 904 is a contact heating element, it may be desirable that the contacting surface of the heating element 904 be made from a material with a high thermal conductivity. In some embodiments, a temperature sensor (not shown) may be included on the heating element 904 to provide temperature information to the controller 902.

The heating element 904 may be sized and shaped to receive an object to be heated. As best shown in FIG. 31, the heating element 904 element has a "U" like shape. This shape allows it to act as holster or shoe for the coupling element 822. A coupling element 822 is shown docked in the heating element 904 in FIG. 30. In some embodiments, a coupling element 822 may be frictionally retained within the heating element 904. In other embodiments, the coupling element 822 and heating element 904 may have a snap-fit or other retaining interface between them.

Once the heating element 904 is in position, a user may use the controller 902 to heat the fusible alloy within the coupling element 822. This may be accomplished by pressing a start/on button on a control panel 908 on the controller 902. The controller 902 may then heat or generate heat with the heating element 904. In some embodiments, the controller 902 may use temperature feedback from a sensor on the heating element 904 so that a specific target temperature or temperature range may be achieved and/or maintained. The target temperature may be sufficient to cause the fusible alloy within the coupling element 822 to become molten. Once molten, the coupling element 822 may be adjusted such that it may be slid over a rod 824. As mentioned above, this adjustment may be necessary because the final location and orientation of a rod 824 (e.g. a transcutaneous rod 24 in FIG. 1) may not be known until after the rod 824 has been implanted during surgery.

As shown, the controller 902 of the heating apparatus 900 includes a display 910. The display 910 may be any suitable variety of display. The display 910 may be used to provide information and indications to a user. For example, the display may indicate that the heating element 904 is on. The display 910 may also provide indication to a user that the fusible alloy is frozen or molten. The display 910 may also communicate error messages, alerts, warnings, instructions, help/troubleshooting information, etc. to a user. Alternatively, a display 910 may not be included on the controller 902. In such embodiments, the controller 902 may include one or more illuminated status indicators which may be used to convey similar information. The controller 902 may additionally include one or more speakers (not shown) to provide audible feedback to a user.

Figure 32:
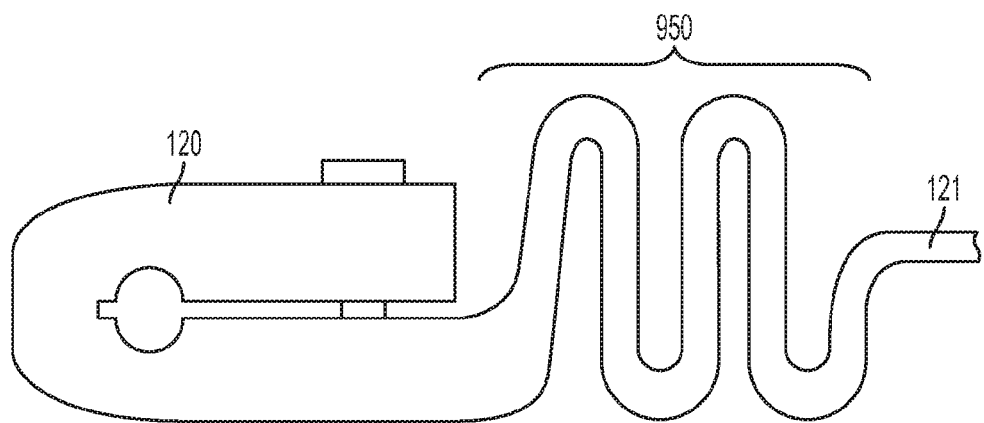
FIGS. 32 & 33 depict example embodiments of a clamp and boom which may be part of a coupling element.
Figure 33:
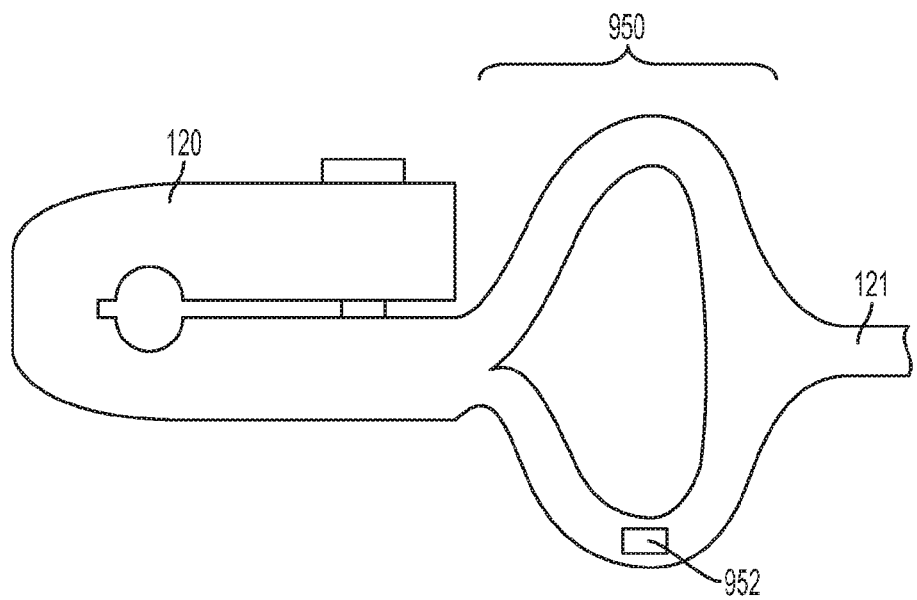

FIGS. 32 & 33 depict example embodiments of a clamp 120 and boom 121 which may be part of a coupling element such as the coupling element 22 shown and described in relation to FIGS. 10-11. In each embodiment, a compliant region 950 is included as a part of the boom 121. The compliant region 950 may be made of any suitable material. The complaint region 950 may act as a spring element. Thus, when a force is applied through the boom 121, the compliant region 950 may act to smooth out the force. In other embodiments, the compliant region 950 may differ in shape or construction. Alternatively, a tension spring (not shown) serving the same purpose may be included and connect the clamp 120 to the boom 121.

As shown in FIG. 33, some embodiments may include a strain gauge 952. The strain gauge 952 may be associated with a suitable portion of the coupling region 950. The strain gauge 952 may be used to measure deformation of the compliant region 950 of the boom 121 as distraction forces are applied to the bone through the boom 121. Data from the strain gauge 952 may be logged and stored in memory of a controller for an external distraction apparatus. This data may be helpful for investigative and research purposes. Additionally, measurements from the strain gauge 952 may be check to see if they are within a predetermined expected range. The expected range may be a range of values which would be expected during proper and safe function of the external distraction apparatus. In the event the value is outside of the predetermined expected range, the apparatus may be caused to enter a fail-safe state, an alert or alarm may be generated, etc.

Figure 34:
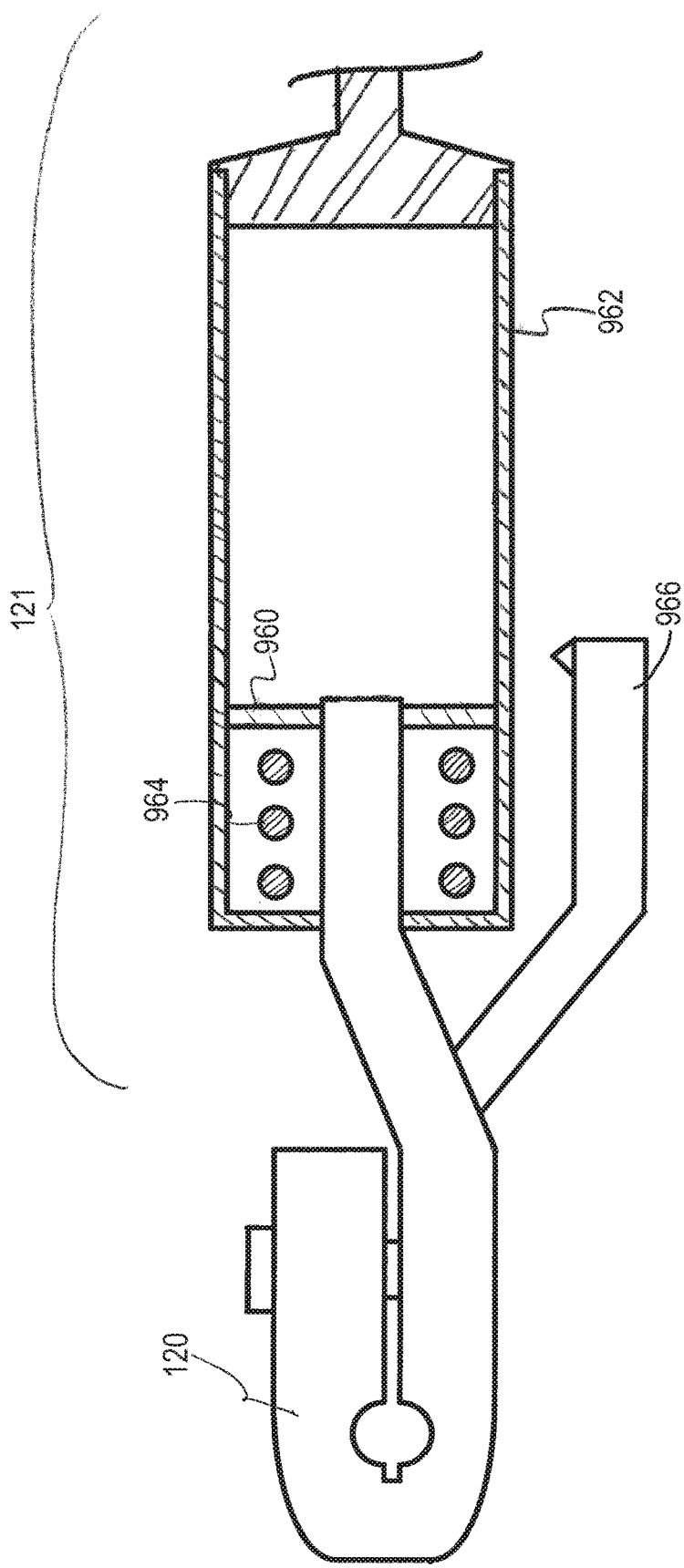
FIG. 34 depicts an example embodiment of a clamp and boom which may be part of a coupling element.

FIG. 34 depicts a representational example embodiment of a clamp 120 and boom 121 which may be part of a coupling element such as the coupling element 22 shown and described in FIGS. 10-11. The boom 121 in FIG. 34 is configured such that it smoothes out any forces which are applied therethrough. As shown the boom 121 includes a piston 960 which travels within a cylinder 962. As shown, the piston 960 may be biased to a position with a bias member which in the example embodiment is a compression spring 964. For illustrative purposes, the piston 960, cylinder 962, and compression spring 964 are shown in cross section.

During a distraction, the portion of the boom 121 to which the cylinder 962 is attached will be caused to move a desired distance. If the clamp 120 is attached to a load (e.g. a transcutaneous rod anchored to a bone) the force applied to cause this movement will not be immediately transmitted to the load. Instead, this force will cause the compression spring 964 to become compressed. Over time, the restoring force of the compression spring 964 will restore the compression spring 964 and consequently move the attached load. Thus the arrangement depicted serves to smooth out distraction forces exerted through the boom 121.

In some embodiments, a visual indicator 966 may also be included. The visual indicator 966 may provide a visual indication of how compressed the compression spring 964 is. In the example embodiment in FIG. 34, the visual indicator 966 is a projection which extends from the portion of the boom 121 which is attached to the clamp 120. The visual indicator 966 includes a pointer which is arranged to point to a reference mark (not shown) or the like on the exterior surface of the cylinder 962. As the compression spring 964 becomes compressed, the visual indicator 966 will move with respect to the cylinder 962. Thus, the pointer on the visual indicator 966 will point to different reference marks depending on the degree of compression of the compression spring 964.

Figure 35:
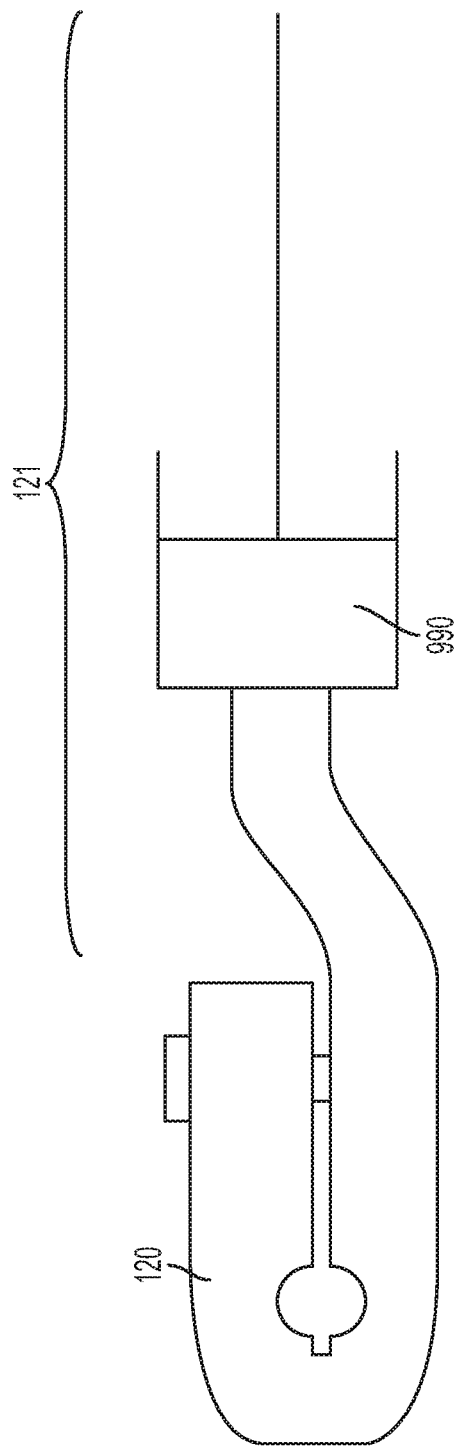
FIG. 35 depicts a representation example embodiment of clamp and boom which may be part of a coupling element.

FIG. 35 depicts another representational example embodiment of a clamp 120 and boom 121 which may be part of a coupling element such as the coupling element 22 shown and described in FIGS. 10-11. As shown, the embodiment in FIG. 35 includes a dashpot 990. The dashpot 990 is shown schematically for purposes of illustration. Including a dashpot 990 may allow the boom 121 to be configured such that it smoothes out any forces which are applied therethrough. Additionally, the dashpot 990 allows the boom 121 to be configured to significantly slow and make more gradual any movement of a load (e.g. a transcutaneous rod anchored to a bone) coupled to the clamp 120. Depending on the dashpot 990 used, the movement may be made gradual enough that near or substantially continuous movement may be achieved.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A craniofacial external distraction apparatus comprising:
   a stationary member configured to be affixed to a head of a patient and having a halo portion, the stationary member configured to be affixed to a first lateral side of the head via a first fixation and to a second lateral side of the head via a second fixation, the halo portion configured to be operatively coupled to the first fixation and the second fixation and traversing therebetween via a front side of the head and superior to eyes of the patient;
   a first upright body configured to be coupled to the stationary member adjacent to the first lateral side of the head, the first upright body inferior to the stationary member;
   a second upright body configured to be coupled to the stationary member adjacent to the second lateral side of the head, the second upright body inferior to the stationary member;
   a first arm member coupled to the first upright body, the first arm member extending anteriorly; and
   a second arm member coupled to the second upright body, the second arm member extending anteriorly, wherein:
   the first arm member includes an anterior portion and a posterior portion,
   the anterior portion is pivotally coupled to the posterior portion via a pivot, and
   the pivot is a harmonic drive assembly.

2. The craniofacial external distraction apparatus according to claim 1, wherein the stationary member and the first and second arms are disposed in spaced relation relative to each other to leave a substantially unobstructed horizontal view by the patient.

3. The craniofacial external distraction apparatus according to claim 1, further comprising:
   a first inferior arm coupled to the first arm member; and
   a second interior arm coupled to the second arm member.

4. The craniofacial external distraction apparatus according to claim 3, wherein the first inferior arm is in sliding engagement with the first arm member.

5. The craniofacial external distraction apparatus according to claim 4, wherein the second inferior arm is in sliding engagement with the second arm member.

6. The craniofacial external distraction apparatus according to claim 1, wherein the first arm member is moveable relative to the first upright body.

7. The craniofacial external distraction apparatus according to claim 1, wherein the first arm member is moveable relative to the first upright body along an axis parallel to a sagittal plane of the head of the patient.

8. The craniofacial external distraction apparatus according to claim 1, wherein the first arm member is moveable relative to the first upright body along an axis parallel to a longitudinal axis of the head of the patient.

\* \* \* \* \*